US010359432B2

(12) United States Patent
Kipps et al.

(10) Patent No.: US 10,359,432 B2
(45) Date of Patent: *Jul. 23, 2019

(54) METHODS FOR DETECTING ANTIBODIES

(71) Applicant: The Regents of the University of California, Oakland, CA (US)

(72) Inventors: Thomas J. Kipps, San Diego, CA (US); Bradley T. Messmer, San Diego, CA (US); Ana B. Sanchez, Encinitas, CA (US); Andrew C. Kummel, San Diego, CA (US); Manuel Ruidiaz, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/981,715

(22) Filed: Dec. 28, 2015

(65) Prior Publication Data

US 2016/0146829 A1 May 26, 2016

Related U.S. Application Data

(63) Continuation of application No. 12/934,624, filed as application No. PCT/US2009/038674 on Mar. 27, 2009, now Pat. No. 9,250,233.

(60) Provisional application No. 61/040,120, filed on Mar. 27, 2008.

(51) Int. Cl.
*G01N 33/543* (2006.01)
*G01N 33/68* (2006.01)
*G01N 33/537* (2006.01)
*G01N 33/94* (2006.01)
*G01N 33/577* (2006.01)
*G01N 33/58* (2006.01)

(52) U.S. Cl.
CPC ....... *G01N 33/6854* (2013.01); *G01N 33/537* (2013.01); *G01N 33/54326* (2013.01); *G01N 33/577* (2013.01); *G01N 33/582* (2013.01); *G01N 33/94* (2013.01)

(58) Field of Classification Search
None
See application file for complete search history.

(56) References Cited

U.S. PATENT DOCUMENTS

| 5,885,577 | A | 3/1999 | Alvarez |
| 6,210,901 | B1 | 4/2001 | Seidel et al. |
| 7,074,888 | B1 | 7/2006 | Miller et al. |
| 9,250,233 | B2 * | 2/2016 | Kipps .................. G01N 33/537 |
| 2005/0084491 | A1 | 4/2005 | Shealy et al. |
| 2005/0208587 | A1* | 9/2005 | Cardoso ............. C07K 16/1063 435/7.1 |
| 2006/0286379 | A1 | 12/2006 | Gao |
| 2011/0124020 | A1 | 5/2011 | Kipps et al. |

FOREIGN PATENT DOCUMENTS

WO   WO 2007/022557   3/2007

OTHER PUBLICATIONS

Dalakas et al., Effect of Alemtuzumab (CAMPATH 1H) in patients with inclusion-body myositis, Brain, 132; 2009, pp. 1536-1544.*
Harlow, E. and Lan D., Antibodies: A Laboratory Manual (1988) Cold Spring Harbor Laboratory Press, Cold Spring Harbor, NY, pp. 23-26.*
Lederman et al. "A single amino acid substitution in a common African allele of the CD4 molecule ablates binding of the monoclonal antibody, OKT4" Mol Immunol. Nov. 1991;28(11): pp. 1171-1181.*
Colman et al. Research im Immunology, 1994; 145(1):pp. 33-36.*
Hale et al., Blood concentrations of alemtuzumab and antiglobulin responsed in patients with chronic lymphocytic leukemia folowing intravenous or subcutaneious routes of adiministration, Blood, Aug. 15, 2004, vol. 104, No. 4, pp. 948-955. (Year: 2004).*
Barenholz et al., A peptide mimetic of the mycobacterial mannosylated lipoarabinomannan: characterization and potential applications, J Med Microbiol., 56:579-586, 2007.
Beum et al., Three new assays for rituximab based on its immunological activity or antigenic properties: analyses of sera and plasma of RTX-treated patients with chronic lymphocytic leukemia and other B cell lymphomas, J. Immunol. Methods, 289(1-2):97-109, 2004.
Blasco et al., Evaluation of a peptide ELISA for the detection of rituximab in serum, J. Immunol. Methods, 325(1-2):127-139, 2007.
Brissette et al., Identification of cancer targets and therapeutics using phage display, Curr Opin Drug Disc Devel., 9(3):363-369 2006.
Carpino et al., The 9-fluorenylmethoxycarbonyl amino-protecting group, J. Org. Chem., 37:3404-3409, 1972.
DeLano et al., Convergent solutions to binding at a protein-protein interface, Science 287(5456):1279-1283, Feb. 18, 2000.
Hale et al., Blood concentrations of alemtuzumab and antiglobulin responses in patients with chronic lymphocytic leukemia following intravenous or subcutaneous routes of administration, Blood, 104(4):948-955, 2004.
Hale, Synthetic peptide mimotope of the CAMPATH-1 (CD52) antigen, a small glycosylphosphatidylinositol-anchored glycoprotein, Immunotechnology 1(3-4):175-187, 1995.

(Continued)

*Primary Examiner* — Gary Counts
(74) *Attorney, Agent, or Firm* — Knobbe, Martens, Olson & Bear LLP

(57) ABSTRACT

Complexes comprising a therapeutic monoclonal antibody and a peptide are provided. In some embodiments, the complexes may comprise a therapeutic monoclonal antibody which is not complexed to an epitope of a target protein and a peptide complexed to the therapeutic monoclonal antibody. In some embodiments, the peptide may have a length of about 5-40 amino acids and may comprise a mimetope recognized by the therapeutic monoclonal antibody, wherein the mimetope comprises a linear sequence of amino acids which is different than a linear sequence of amino acids in the epitope of the target protein.

17 Claims, 10 Drawing Sheets

Specification includes a Sequence Listing.

(56) References Cited

OTHER PUBLICATIONS

Jiang et al., A Novel Peptide Isolated from a Phage Display Peptide Library with Trastuzumab Can Mimic Antigen Epitope of HER-2, J Biol Chem. 280(6):4656-4662, 2005.

Jilani et al., Alemtuzumab: validation of a sensitive and simple enzyme-linked immunosorbent assay, Leuk. Res., 28(12):1255-1262, 2004.

Maloney et al., IDEC-C2B8 (rituximab) anti-CD20 monoclonal antibody therapy in patients with relapsed low-grade non-Hodgkin's lymphoma, Blood, 90(6):2188-2195, Sep. 15, 1997.

Manshouri et al., Circulating CD20 is detectable in the plasma of patients with chronic lymphocytic leukemia and is of prognostic significance, Blood, 101(7):2507-2513, Apr. 1, 2003.

Merrifield, Solid phase peptide synthesis. I. The synthesis of a tetrapepide, J. Amer. Chem. Soc., 85:2149-2154, 1963.

Messmer et al., Specific blocking to improve biopanning in biological samples such as serum and hybridoma supernatants, Biotechniques 30(4):798-802, Apr. 2001.

Messmer et al., Two human neonatal IgM antibodies encoded by different variable-region genes bind the same linear peptide: Evidence for a stereotyped repertoire of epitope recognition, J. Immunol., 162(4):2184-2192, 1999.

Montagna et al., A new sensitive enzyme-linked immunosorbent assay (elisa) for alemtuzumab determination: development, validation and application, Int. J. Immunopathol., Pharmacol. 20(2):363-371, 2007.

Mulvaney et al., Incorporating fluorescent dyes and quantum dots into magnetic microbeads for immunoassays, BioTechniques. 36(4):602-609, 2004.

Perosa et al., Identification of an antigenic and immunogenic motif expressed by two 7-mer rituximab-specific cyclic peptide mimotopes: implication for peptide-based active immunotherapy, J. Immunol. 179(11):7967-7974, 2007.

Rebello et al., Pharmacokinetics of CAMPATH-1H: assay development and validation, J. Immunol. Methods, 260(1-2):285-302, 2002.

Rohr et al., Immunoassay employing surface-enhanced raman spectroscopy, Analytical Biochemistry, 182:388-398, 1989.

Shin et al., Combinatorial solid phase peptide synthesis and bioassays, J. Biochem. and Mol. Biol., 38(5):517-525, Sep. 2005.

Stewart et al., Solid phase Peptide Synthesis, Rockford, IL: Pierce Chemical Company, Table of Contents, 7 pages, 1984.

Tan et al., Pharmacokinetics of cetuximab after administration of escalating single dosing and weekly fixed dosing in patients with solid tumors, Clin. Cancer Res., 12(21):6517-6522, 2006.

Williams et al., Thrice-weekly low-dose rituximab decreases CD-20 loss via shaving and promotes enhanced targeting in chronic lymphocytic leukemia, J. Immunol., 177(10):7435-7443, 2006.

International Search Report and Written Opinion dated Dec. 24, 2009 for Application No. PCT/US2009/038674, filed Mar. 27, 2009.

\* cited by examiner (SEQ ID NO: 1) Cp-1    A C G S L S P S S C
(SEQ ID NO: 2) Cp-3    A C K S Q S P S A C
(SEQ ID NO: 3) Cp-11   A C G S T S P S S C
(SEQ ID NO: 4) RTX-11  A C P Y A N P S M C
(SEQ ID NO: 5) RTX-10  A C P Y S N P S L C
FIG. 1
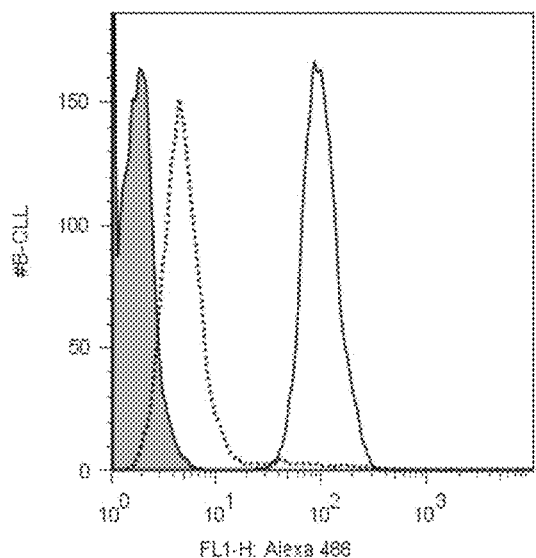
FIG. 2A
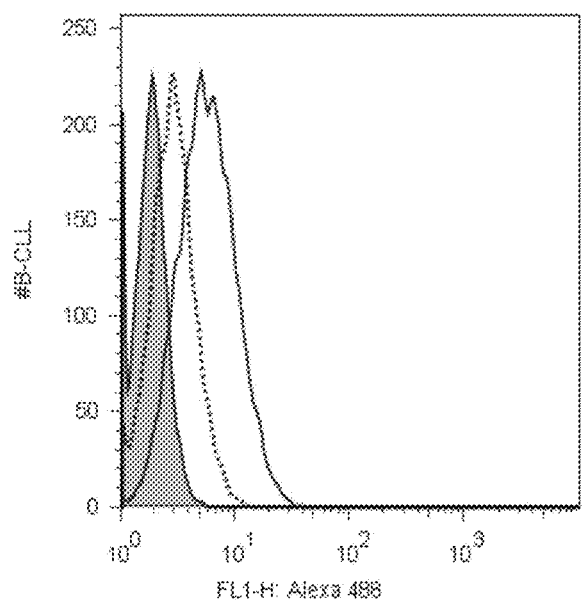
FIG. 2B

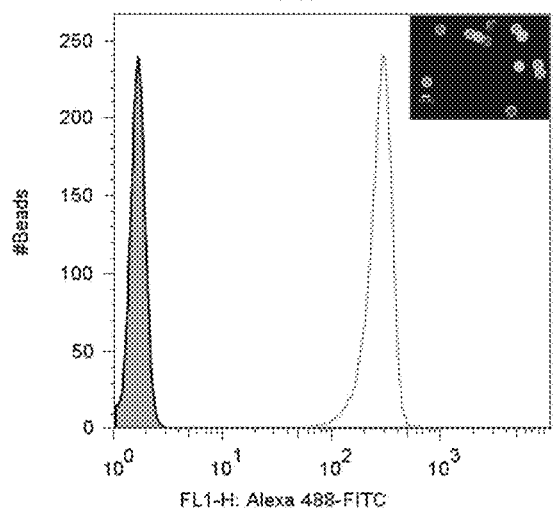
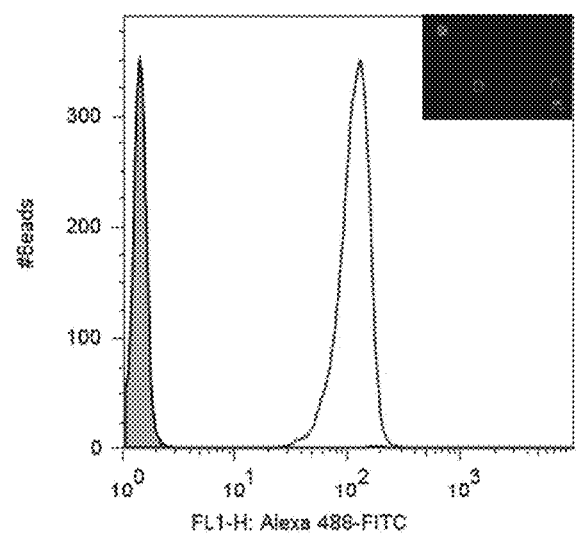
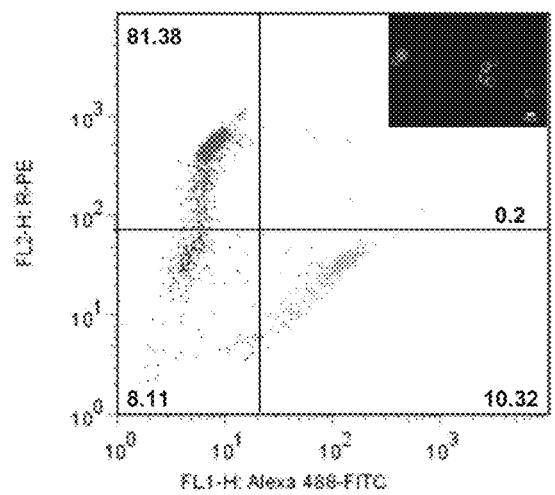

| | | |
|---|---|---|
| (SEQ ID NO: 11) | Avastin-02 | CIPSIREWC |
| (SEQ ID NO: 12) | Avastin-01 | CMSPFDHSC |
| (SEQ ID NO: 13) | Avastin-05 | CFLRSGLPC |
| (SEQ ID NO: 14) | Avastin-07 | CTDTATALC |
| (SEQ ID NO: 15) | Herceptin-01 | CVDHHLDHC |
| (SEQ ID NO: 16) | HuMax-01 | CAPGFLPVC |
| (SEQ ID NO: 17) | HuMax-04 | CLWPPSPVC |
| (SEQ ID NO: 18) | HuMax-05 | CSWPPSPVC |
| (SEQ ID NO: 19) | HuMax-06 | CSYPPAPVC |

FIG. 8

| SAMPLE ID | Mean, FL1-H | Median, FL1-H |
|---|---|---|
| Redbeads-10 | 492.89 | 483.15 |
| Redbeads-1.0 | 94.40 | 74.32 |
| Redbeads-0.5 | 49.09 | 36.19 |
| Redbeads-0.1 | 5.69 | 5.26 |
| Redbeads-0.0 | 2.11 | 1.68 |

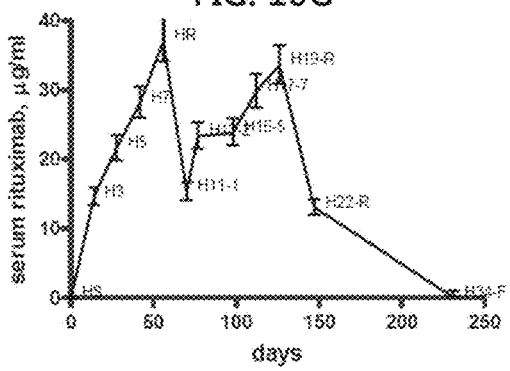
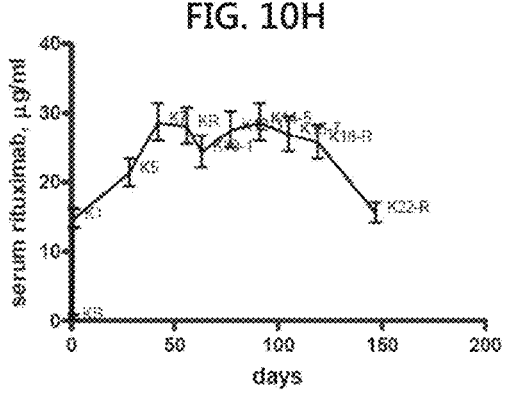
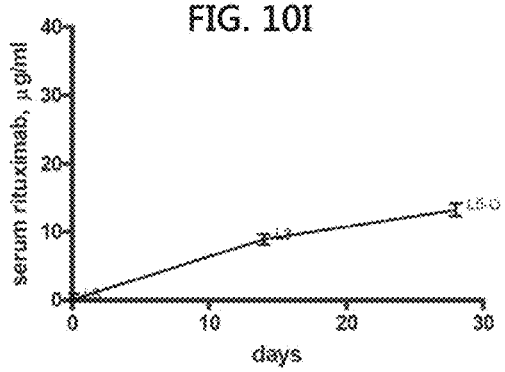
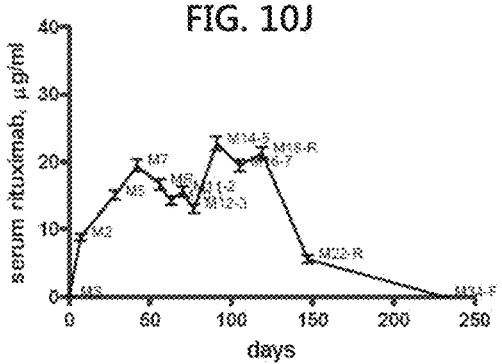
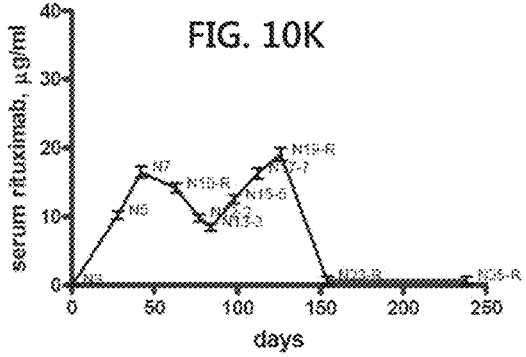
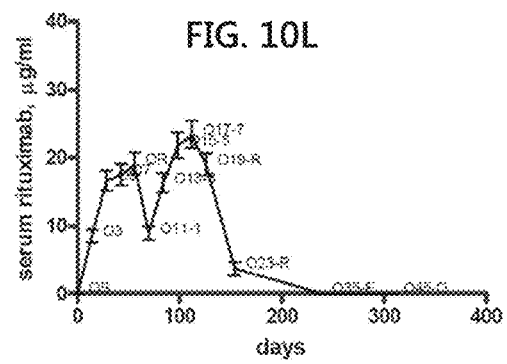

METHODS FOR DETECTING ANTIBODIES

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57. This application is a continuation of U.S. application Ser. No. 12/934,624 filed Sep. 24, 2010, now U.S. Pat. No. 9,250,233, issued Feb. 2, 2016; which is the 35 USC § 371 National Stage application of International Application No. PCT/US2009/038674 filed Mar. 27, 2009; which claims the benefit under 35 USC § 119(e) to U.S. Application Ser. No. 61/040,120 filed Mar. 27, 2008. The disclosure of each of the prior applications is considered part of and is incorporated by reference in the disclosure of this application in its entirety.

STATEMENT REGARDING FEDERALLY SPONSORED R&D

This invention was made with government support under Grant No. CA 119335 awarded by the National Institutes of Health. The government has certain rights in the invention.

REFERENCE TO SEQUENCE LISTING, TABLE, OR COMPUTER PROGRAM LISTING

The present application is being filed along with a Sequence Listing in electronic format. The Sequence Listing is provided as a file entitled UCSD094-001C1_Sequence_Listing, created Dec. 21, 2015, which is 5 KB in size. The information in the electronic format of the Sequence Listing is incorporated herein by reference in its entirety.

BACKGROUND OF THE INVENTION

Field of the Invention

The invention relates generally to the detection of antibodies and more specifically to methods for detection of antibodies including a generalized approach applicable to any antibody along with antibody specific assays developed using the approach.

Background Information

Antibodies and other polypeptides are widely used in a variety of applications, from use as therapeutic agents to use as reagents in biological assays. The ability to detect and quantify antibodies is a key aspect in many of the applications for which they are currently used. For instance, detection of antibodies and other protein therapeutics in a biological sample is key in medical applications requiring determination of diagnostic and/or prognostic factors. However, determining the pharmacokinetics of a particular antibody can be problematic, especially where the detection is performed against a high background, as in a biological sample.

The need for accurate pharmacokinetic determinations is acute, but has not yet been met by existing methodologies. Dosing schedules and routes of administration for antibodies are developed with many uncertainties and are often refined through pre-clinical and clinical studies where the need for simple and reliable pharmacokinetic assays is acute. The specific biology of a given antibody target can also lead to additional complications from the conventional dose escalation paradigm. For instance, there have been reports of cell free CD20 in the plasma of chronic lymphoid leukemia (CLL) patients (Manshouri et al., *Blood*, 101(7):2507, 2003). Other reports have suggested that CD20 may be "shaved" from CLL cells consequent to rituximab treatment (Williams et al., *J. Immunol.*, 177(10):7435, 2006), which may or may not affect the detection of free rituximab (Beum et al., *J. Immunol. Methods*, 289(1-2):97, 2004). Accordingly, detection of noncomplexed antibody is a critical factor for reliable prognostics and diagnostics.

To date, several approaches have been used to study the pharmacokinetics of these treatments, in part to determine diagnostic and prognostic factors, such as progression of cancer. One approach entails making the target molecule recombinantly for use in assays such as sandwich enzyme-linked immunosorbent assays (ELISAs) (Tan et al., *Clin. Cancer Res.*, 12(21):6517, 2006). However, it may not always be possible to generate the recognized portion of the target molecule and it is expensive and cumbersome to generate large amounts of recombinant protein.

An alternative approach involves generating peptides designed from the target antigen sequence, which has been met with limited success (Blasco et al., *J. Immunol. Methods*, 325(1-2):127, 2007). Another alternative is to express the target molecule on a cell line by transfection, using flow cytometry to assess the binding of the desired antibody (Rebello et al., *J. Immunol. Methods*, 260(1-2):285, 2002). This method has been used for the antibody therapeutic alemtuzumab (anti-CD52), but is difficult to develop, requires skilled personnel to execute, and has limited sensitivity (Hale et al., *Blood*, 104(4):948, 2004).

In yet another approach, ELISA assays have been developed that use antibodies specific for the therapeutic antibody (Montagna et al., *Int. J. Immunopathol., Pharmacol.* 20(2):363, 2007). The antibodies used for this purpose are either anti-idiotypic (Maloney et al., *Blood*, 90(6):2188, 1997) or specific for residual non-human sequences of the therapeutic antibody, as was the case with alemtuzumab (Jilani et al., *Leuk. Res.*, 28(12):1255, 2004). However, each of these approaches is technically demanding and has limited sensitivity when used in biologic samples because of high background. The latter approach in particular will not work with fully humanized antibodies.

In light of the limitations of developing assays for detection of specific antibodies or other peptide therapeutics, a need exists for a single, inexpensive generalized approach of assay development which may be used for development of highly specific assays for a variety of antibodies or other recombinant proteins. Such assays will not only be useful in pharmacokinetic studies but, due to their high sensitivities, can also be applied to diagnosis and prognosis of diseases associated with the presence or absence of the targeted molecules in a biological sample.

SUMMARY OF THE INVENTION

The present invention relates to a method of detecting any antibody or other recombinant protein, such as an antibody fragment, in a given sample, where the targeted molecule is not complexed with antigen. The method includes a standardized approach of assay development which is applicable to any antibody and provides highly specific assays for individual or multiple antibodies.

Accordingly, the present invention provides a method for detecting an antibody not complexed to antigen in a biological sample suspected of containing such antibody. The method includes directly synthesizing one or more peptides having a length of about 5-15 amino acids and including a mimetope recognized by the antibody directly on a solid support. The peptide-support conjugate is then contacted with the biological sample in suitable conditions to allow binding of the bound peptides with the antibody to form an antibody-peptide complex. Subsequently, the antibody-peptide complex is detected. Detection of the complex may occur at antibody concentrations below 500 ng/ml of the biological sample.

In various embodiments, the mimetope is identified from a phage-displayed peptide library. Identifying the mimetope by screening of the library allows for mimetopes to be identified that binds specifically with the antigen binding site of the antibody. In related embodiments, detection of the antibody-peptide complex is performed by detection of a detectable label marking the antibody-peptide complex using a suitable detection assay.

In a particularly preferred embodiment, the detection assay is performed on magnetized beads modified to include reporter molecules, such as fluorophores. Such assays are susceptible to automation for large-scale analysis of samples.

In various aspects, the antibody is a monoclonal antibody, such as, but not limited to alemtuzumab, bevacizumab, rituximab, trastuzumab, and zanolimumab.

BRIEF DESCRIPTION OF THE DRAWINGS

FIG. 1 is an illustration of phage-displayed peptide sequences recovered from panning against alemtuzumab (top; Cp-1 (SEQ ID NO:1); Cp-3 (SEQ ID NO:2); and Cp-11 (SEQ ID NO:3)) and rituximab (bottom; RTX-11 (SEQ ID NO:4); and RTX-10 (SEQ ID NO:5)). Phage-displayed libraries were panned against the monoclonal antibodies for three rounds, after which individual phage clones were picked and sequenced. The deduced sequences of the displayed peptides are shown aligned, with amino acid identity boxed. Cp-1 (SEQ ID NO:1) and RTX-10 (SEQ ID NO:5) were selected for further analysis as synthetic peptides.

FIGS. 2A and 2B include graphical illustrations showing peptide inhibition of CLL cell staining. Fluorescently labeled alemtuzumab (FIG. 2A) or rituximab (FIG. 2B) was incubated with primary CLL cells and evaluated by flow cytometry (solid line). As expected, robust staining with alemtuzumab was seen while the staining for CD20 with rituximab was weak. When peptides pCp-1B (SEQ ID NO: 7) or pRTX-10B (SEQ ID NO: 8) were added at a 25,000 molar excess (dashed lines), the cell labeling was largely abrogated. The shaded histogram represents staining with labeled human IgG.

FIGS. 5A and 5B include graphical illustrations showing flow cytometry analysis of fluorescently tagged mAb. FIG. 5A shows analysis by flow cytometry of 1 µg alemtuzumab labeled using Zenon kit Alexa 488™ and incubated with $6 \times 10^4$ Cp-1 (SEQ ID NO:1) coated beads. FIG. 5B shows analysis by flow cytometry of 1 µg rituximab labeled using Zenon kit R-PE™ and incubated with $6 \times 10^4$ RTX-10 (SEQ ID NO:5) coated beads and analyzed following the same protocol described for FIG. 5A. FIG. 5C is a graphical illustration showing that the beads and labeled antibodies of FIGS. 5A and 5B could be mixed without cross reaction between the mAb and the non-cognate peptide bead.

FIG. 6A shows an x-axis scale extending to $10^3$. FIG. 6B is an expanded version of the graph shown in FIG. 6A in which the x-axis scale is from 0 to 1000.

FIG. 7A shows the binding of the mAb alemtuzumab (Campath™). FIG. 7B shows the binding of Fab fragments of alemtuzumab (Campath™). FIG. 7C shows the binding of the mAb rituximab. FIG. 7D shows the binding of Fab fragments of rituximab.

FIG. 8 is an illustration showing phage-displayed peptide sequences recovered from panning against three different mAbs. Phage-displayed peptide sequences recovered from panning against bevacizumab (Avastin™) included Avastin™-02 (SEQ ID NO:11), Avastin™-01 (SEQ ID NO:12), Avastin™-05 (SEQ ID NO:13), and Avastin™-07 (SEQ ID NO:14). Phage displayed-peptide sequences recovered from panning against trastuzumab (Herceptin™) included Herceptin™-01 (SEQ ID NO: 15). Phage displayed peptide sequences recovered from panning against zanolimumab (HuMax™) included HuMax™-01 (SEQ ID NO:16), HuMax™-04 (SEQ ID NO:17), HuMax™-05 (SEQ ID NO:18), and HuMax™-06 (SEQ ID NO:19). Phage displayed-libraries were panned against the monoclonal antibodies for four rounds, after which individual phage clones were picked and sequenced.

FIGS. 10A to 10L include graphical representations showing serum rituximab concentration in patients being treated with the mAb at various time points over the course of treatment. Each of FIGS. 10A to 10L show a plot of serum rituximab concentration at different time points for a given patient undergoing treatment with the mAb.

DETAILED DESCRIPTION OF THE INVENTION

Figure 3A:
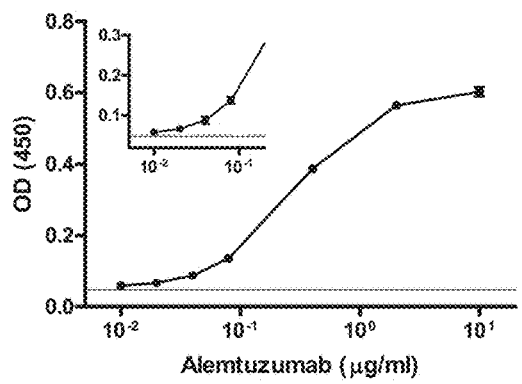
FIGS. 3A and 3B include graphical illustrations showing alemtuzumab (FIG. 3A) and rituximab (FIG. 3B) detection by peptide ELISA. Biotinylayed peptides were bound onto neutravidin coated ELISA plates. Both alemtuzumab and rituximab antibodies were diluted in TBST. Each value shows the mean (±S.D.) of triplicates. The solid line indicates the mean of the buffer control and the dashed line represents the mean+10 times the SD of the buffer control.

The present invention is based, in part, on the development of an innovative method for detection of any antibody utilizing a standardized approach applicable to any antibody which provides highly specific assays specific for individual or multiple antibodies. The present invention enables improved pharmacokinetic analysis during development and clinical use of antibody based therapies as well as determination of diagnostic and/or prognostic factors.

Before the present composition, methods, and treatment methodology are further described, it is to be understood that this invention is not limited to particular compositions, methods, and experimental conditions described, as such compositions, methods, and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "the method" includes one or more methods, and/or steps of the type described herein which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described.

The present invention provides a method for detecting an antibody not complexed to antigen in a biological sample suspected of containing such antibody. The method includes directly synthesizing one or more peptides having a length of about 5-15 amino acids and including a mimetope recognized by the antibody on a solid support. The peptides preferably include mimetopes recognized by the antibody of interest by screening phage-displayed libraries. The peptide-support conjugate is then contacted with the biological sample in suitable conditions to allow binding of the bound peptides with the antibody to form an antibody-peptide complex. Subsequently, the antibody-peptide complex is detected.

In various embodiments, peptides are directly synthesized on the solid support by solid-phase peptide synthesis (SPPS). Introduced in 1963 (Merrifield, *J. Amer. Chem. Soc.*, 85:2149-2154, 1963), the original concept of SPPS has lead to several conventional methods of directly synthesizing peptides on solid supports that are suitable for use with the present invention. In general, two strategies for the synthesis of peptide chains by SPSS are known in the art; stepwise solid-phase synthesis, and solid-phase fragment condensation. In stepwise SPPS, the C-terminal amino acid in the form of an N-α-protected side-chain, the protected reactive derivative is covalently coupled either directly or by means of a suitable linker to a "solid" support, which is typically swollen in an organic solvent. The N-α-protective group is removed, and the subsequent protected amino acids are added in a stepwise fashion.

When the desired peptide chain length has been obtained, the side-chain protective groups are removed, and the peptide, may or may not be cleaved from the support surface. Removal of the protective group and cleavage may be done in separate steps or at the same time. For use in the invention, however, it will be appreciated that the peptide need not be, and preferably is not, cleaved from the solid support, which can be used as the solid phase for the assays described herein.

In solid-phase fragment condensation, the target sequence is assembled by consecutive condensation of fragments on a solid support using protected fragments prepared by stepwise SPPS. Additional conventional methods of performing SPSS include split and mix synthesis, reagent mixture synthesis, and in situ parallel synthesis (Shin et al., *J. Biochem. and Mol. Biol.*, 38(5):517-525, 2005).

Typically, two coupling strategies are used to perform SPPS, tert-butyloxycarbonyl (Boc) and fluorenylmethyloxycarbonyl (Fmoc), which are based on the use of different N-α-protective groups and matching side-chain protective groups. The Boc approach utilizes Boc as the N-α-protective group (Merrifield, *J. Amer. Chem. Soc.*, 85:2149-2154, 1963), versus Fmoc (Carpino et al., *J. Org. Chem.*, 37:3404-3409, 1972). While the Boc and Fmoc strategies have been used for essentially all current practical peptide synthesis, other N-α-protective groups have been proposed (Stewart et al., Solid phase Peptide Synthesis, Pierce Chemical Company, 1984).

Conveniently, phage-displayed peptide libraries can be used to identify mimetope peptides that bind to the antigen binding site of antibodies in a specific and selective fashion. While it is theoretically possible that peptides that bind to the constant region of an antibody could be enriched, and would thus lack specificity, this is not usually the case. The constant regions of antibodies are generally refractory to short peptide libraries and even if they are selected, simple competitive blocking schemes can be used (Messmer et al., *Biotechniques* 30(4):798, 2001). Constant region binding peptides have been selected from longer libraries (DeLano et al., *Science* 287(5456):1279, 2000). Peptide mimetopes identified using the approach described herein are expected to be specific and compete with the target cell surface antigen for antibody binding as confirmed by the data presented herein.

As discussed in detail further below, to demonstrate the robustness of the invention, peptide sequences recognized by alemtuzumab (anti-CD52) or rituximab (anti-CD20) were selected from phage-displayed peptide libraries. Synthetic biotinylated peptides were used in immunoassays, such as enzyme linked immunoadsorbant assays (ELISA) and had a sensitivity of less than 0.05 µg/ml in saline buffer, but the functional sensitivity in serum was limited to approximately 1 ug/ml by the need to dilute samples to reduce background. Additional immunoassays were developed by the preferred methods described herein in which the peptides were synthesized on the surface of 10 µm diameter beads.

A critical factor in assays utilizing surface-bound peptides is accessibility of the surface peptide to the target molecule. Another critical factor is presenting the peptide on the solid support such that it retains its specific binding affinity for its target molecule (e.g., binding partner). Accordingly, the methods described herein allow for assay formats in which the peptides including the identified mimetopes are 1) presented on the surface of solid supports such that binding affinity of the peptides for a given antibody is not reduced when the peptide is linked to the solid support; and 2) the peptide is affixed such that it is accessible to the antibody. In an exemplary aspect, the peptides are synthesized directly on the surface of small beads using conventional SPPS techniques known in the art and discussed herein. Typically, beads are treated with functional units or linkers suitable for synthesis of peptide chains, and importantly the peptides remain uncleaved after synthesis; e.g., the peptide remains covalently attached to the bead.

Antibody binding was detected by fluorochrome labeled secondary antibodies via flow cytometry. There was negligible background signal on the beads, even in neat serum. The functional sensitivity using peptide-beads was less than 0.05 µg/ml. The enhanced sensitivity of the bead based assay is ideal for detecting very low levels of the target antibody, while the ELISA is sufficient when the target antibody concentrations are greater than 1.0 ug/ml. The methods outlined herein are can be used for detection of any mAb.

As used herein, a "mimetope" is a determinant which is recognized by the same binding molecule, such as an antibody, as a particular "epitope" but which has a different composition from the "epitope." For example, a binding molecule can be an antibody which recognizes (i.e., binds to) an epitope comprising a linear sequence of amino acids. A "mimetope" of this epitope comprises a different linear sequence of amino acids but which is still recognized by the same antibody.

The terms "polypeptide" and "peptide" are used broadly to refer to macromolecules comprising linear polymers of natural or synthetic amino acids. Polypeptides may be derived naturally or synthetically by standard methods known in the art. While the term "polypeptide" and "peptide" are synonymous, the term "polypeptide" generally refers to molecules of greater than 40 amino acids, while the term "peptide" generally refers to molecules of 2 to 40 amino acids.

Peptide libraries displayed on bacteriophage may be used to identify peptide epitopes, or mimetopes, recognized by antibodies. When short peptides, from about 5 to 15 amino acids or about 7 to 12 amino acids, are screened, the selected peptides almost invariably bind to the antigen-binding site of the antibody and are competed by the natural ligand (Messmer et al., *J. Immunol.*, 162(4):2184, 1999).

This property makes such libraries ideal for the selection of epitope targets that can be used in ELISA or other immunoassays. Accordingly, in various embodiments, the peptides derived from screening phage-displayed libraries have a length of about 2 to 40, 3 to 20, 5 to 15, or 7 to 12 amino acids.

The phage-displayed peptide libraries utilized in the present invention are commonly used by those skilled in the art and provide a powerful method in identifying peptide agonists and antagonists. In typical display libraries, random peptide sequences are displayed by fusion with coat proteins of filamentous phage. Typically, the displayed peptides are affinity-eluted against an antibody-immobilized extracellular domain of a receptor. The retained phages may be enriched by successive rounds of affinity purification and repropagation. The best binding peptides are typically sequenced to identify key residues within one or more structurally related families of peptides.

As used herein, the term "antibody" is used broadly herein to refer to a polypeptide or a protein complex that can specifically bind an epitope of an antigen or mimetope thereof. An antibody includes an intact antibody, or a binding fragment thereof that competes with the intact antibody for specific binding and includes chimeric, humanized, fully human, and bispecific antibodies. Binding fragments include, but are not limited to, Fab, Fab', F(ab)$_2$, Fv, and single-chain antibodies. In various embodiments, the antibody may be monoclonal or polyclonal.

In an exemplary aspect, the present invention relates to detection of monoclonal antibodies. Monoclonal antibodies are typically used in therapeutic applications, such as in the treatment of cancer. As used herein, a "monoclonal antibody" may be from any origin, such as mouse or human, including a chimeric antibody thereof. Additionally, the antibody may be humanized.

Examples of monoclonal antibodies include, but are not limited to, 3F8, Abagovomab, Abatacept, Abciximab, ACZ885, Adalimumab, Adecatumumab, Afelimomab, Aflibercept, Afutuzumab, Alacizumab, Alemtuzumab, Altumomab, Anatumomab, Anrukinzumab, Apolizumab, Arcitumomab, Aselizumab, Atlizumab, Atorolimumab, Bapineuzumab, Basiliximab, Bavituximab, Bectumomab, Belatacept, Belimumab, Bertilimumab, Besilesomab, Bevacizumab, Biciromab, Bivatuzumab, Blinatumomab, Canakinumab, Cantuzumab, Capromab, Catumaxomab, Cedelizumab, Certolizumab, Cetuximab Erbitux, Citatuzumab, Cixutumumab, Clenoliximab, CNTO 1275 (=ustekinumab), CNTO 148 (=golimumab), Conatumumab, Dacetuzumab, Dacliximab (=daclizumab), Daclizumab, Denosumab, Detumomab, Dorlimomab, Dorlixizumab, Ecromeximab, Eculizumab, Edobacomab, Edrecolomab, Efalizumab, Efungumab, Elsilimomab, Enlimomab, Epitumomab, Epratuzumab, Erlizumab, Ertumaxomab, Etanercept, Etaracizumab, Exbivirumab, Fanolesomab, Faralimomab, Felvizumab, Figitumumab, Fontolizumab, Foravirumab, Galiximab, Gantenerumab, Gavilimomab, Gemtuzumab, Golimumab, Gomiliximab, Ibalizumab, Ibritumomab, Igovomab, Imciromab, Infliximab Remicade, Inolimomab, Inotuzumab ozogamicin, Ipilimumab, Iratumumab, Keliximab, Labetuzumab, Lebrilizumab, Lemalesomab, Lerdelimumab, Lexatumumab, Libivirumab, Lintuzumab, Lucatumumab, Lumiliximab, Mapatumumab, Maslimomab, Matuzumab, Mepolizumab, Metelimumab, Milatuzumab, Minretumomab, Mitumomab, Morolimumab, Motavizumab, Muromonab, MYO-029, Nacolomab, Naptumomab, Natalizumab, Nebacumab, Necitumumab, Nerelimomab, Nimotuzumab, Nofetumomab, Ocrelizumab, Odulimomab, Ofatumumab, Omalizumab, Oportuzumab, Oregovomab, Otelixizumab, Pagibaximab, Palivizumab, Panitumumab, Panobacumab, Pascolizumab, Pemtumomab, Pertuzumab, Pexelizumab, Pintumomab, Priliximab, Pritumumab, PRO 140, Rafivirumab, Ramucirumab, Ranibizumab, Raxibacumab, Regavirumab, Reslizumab, Rilonacept, Rituximab, Robatumumab, Rovelizumab, Rozrolimupab, Ruplizumab, Satumomab, Sevirumab, Sibrotuzumab, Siltuximab, Siplizumab, Solanezumab, Sonepcizumab, Sontuzumab, Stamulumab, Sulesomab, Tacatuzumab, Tadocizumab, Talizumab, Tanezumab, Taplitumomab, Tefibazumab, Telimomab, Tenatumomab, Teneliximab, Teplizumab, TGN1412, Ticilimumab (=tremelimumab), Tigatuzumab, TNX-355 (=ibalizumab), TNX-650, TNX-901 (=talizumab), Tocilizumab, Toralizumab, Tositumomab, Trastuzumab, Tremelimumab, Tucotuzumab, Tuvirumab, Urtoxazumab, Ustekinumab, Vapaliximab, Vedolizumab, Veltuzumab, Vepalimomab, Visilizumab, Volociximab, Votumumab, Zalutumumab, Zanolimumab, Ziralimumab, and Zolimomab.

In one embodiment, the present invention relates to detection of the monoclonal antibody alemtuzumab. As shown in FIG. 1 and the following examples, peptides including mimetopes for alemtuzumab were determined by panning against alemtuzumab. Accordingly, for detection of alemtuzumab the peptides utilized for conjugating to solid supports include Cp-1 (SEQ ID NO:1), Cp-3 (SEQ ID NO:2) and Cp-11 (SEQ ID NO:3).

In another embodiment, the present invention relates to detection of the monoclonal antibody rituximab. As shown in FIG. 1 and the following examples, peptides including mimetopes for rituximab were determined by panning against rituximab. Accordingly, for detection of rituximab the peptides utilized for conjugating to solid supports include RTX-11 (SEQ ID NO:4) and RTX-10 (SEQ ID NO:5).

In another embodiment, the present invention relates to detection of the monoclonal antibody bevacizumab. As shown in FIG. 8, peptides including mimetopes for bevacizumab were determined by panning against bevacizumab. Accordingly, for detection of bevacizumab the peptides utilized for conjugating to solid supports include Avastin™-02 (SEQ ID NO:11), Avastin™-01 (SEQ ID NO:12), Avastin™-05 (SEQ ID NO:13), and Avastin™-07 (SEQ ID NO:14).

In another embodiment, the present invention relates to detection of the monoclonal antibody trastuzumab. As shown in FIG. 8, peptides including mimetopes for trastuzumab were determined by panning against trastuzumab. Accordingly, for detection of trastuzumab the peptides utilized for conjugating to solid supports include Herceptin™-01 (SEQ ID NO:15).

In another embodiment, the present invention relates to detection of the monoclonal antibody zanolimumab. As shown in FIG. 8, peptides including mimetopes for zanolimumab were determined by panning against zanolimumab. Accordingly, for detection of zanolimumab the peptides utilized for conjugating to solid supports include HuMax™-01 (SEQ ID NO:16), HuMax™-04 (SEQ ID NO:17), HuMax™-05 (SEQ ID NO:18), and HuMax™-06 (SEQ ID NO:19).

As discussed herein, peptides are bound to or, most preferably, synthesized directly on solid supports and utilized in the assays without cleavage of the synthesized peptides. The sequence of the peptides of interest can identified by sequencing the relevant portion; e.g., the binding site identified in the panned phage genomes for synthesis and binding to, or synthesis directly on, a solid support.

The term "solid support" refers to any solid phase material upon which a polypeptide is synthesized or attached, such as conjugation via covalent bond. Solid support encompasses terms such as "resin", "solid phase", and "support". A solid support may be composed of organic polymers such as polystyrene, polyethylene, polypropylene, polyfluoroethylene, polyethyleneoxy, and polyacrylamide, as well as co-polymers and grafts thereof. A solid support may also be inorganic, such as glass, silica, controlled-pore-glass (CPG), or reverse-phase silica. The configuration of a solid support may be in the form of beads, spheres, particles, granules, or a surface. Surfaces may be planar, substantially planar, or non-planar. Solid supports may be porous or non-porous, and may have swelling or non-swelling characteristics. A solid support may be configured in the form of a well, depression or other vessel.

In various embodiments, the peptides may be directly attached or synthesized directly on a solid support. As such, the peptides may include a short linker or spacer peptide to facilitate attachment or synthesis. For example, a typical linker or spacer is about 1, 2, 3, 4, 5, 6, 7, 8, 9, or 10 amino acids in length.

Functional groups for attachment of peptides can be incorporated into the polymer structure of solid support by conventional means, including the use of monomers that contain the functional groups, either as the sole monomer or as a co-monomer. Examples of suitable functional groups are amine groups ($-NH_2$), ammonium groups ($-NH_{3+}$ or $-NR_{3+}$), hydroxyl groups ($-OH$), carboxylic acid groups ($-COOH$), and isocyanate groups ($-NCO$). Useful monomers for introducing carboxylic acid groups into polyolefins, for example, are acrylic acid and methacrylic acid.

Attachment of the peptide to the solid phase surface can be achieved by electrostatic attraction, specific affinity interaction, hydrophobic interaction, or in an exemplary fashion covalent bonding. Linkers can be used as a means of increasing the density of reactive groups on the solid phase surface and decreasing steric hindrance to increase the range and sensitivity of the assay. Examples of suitable useful linkers are polylysine, polyaspartic acid, polyglutamic acid and polyarginine.

Typically, the type of solid support surface utilized is determined by the method desired for detection of the antibody-peptide complex. For instance, in one embodiment, peptides may be conjugated with a multi-well plate (e.g., 96 well) for detection using ELISA. Alternatively, in another embodiment, peptides may be conjugated with beads to facilitate detection by flow cytometry.

In one embodiment, the peptides are directly attached or synthesized directly on beads. While the bead may be manufactured from any suitable material known in the art, in an exemplary embodiment, the bead is made of a resin that is a graft copolymer of a crosslinked polystyrene matrix and polyethylene glycol (PEG), such as TentaGel™ beads (Rapp Polymere GmbH). As discussed herein, it was determined that, surprisingly, peptides synthesized directly on TentaGel™ beads have extremely low background levels in neat or marginally diluted samples, ideal for supporting a flow cytometry based approach for sensitive detection of antibodies in plasma or serum. The use of beads in conjunction with a flow cytometry approach result in unexpectedly low background binding, even in high concentrations of serum. Without being bound to any theory, PEG, a main constituent of the bead material, is often used to limit non-specific adsorption of proteins to surfaces and particles, which may explain the extremely low backgrounds observed with the beads. The bead assay format utilizing flow cytometry may be likened to the use of a cell line expressing the target antigen, but is simpler and easier to standardize. Peptide ligands are ideal since they can be made cheaply at high purity and can be synthesized directly on the beads.

In various embodiments, beads of different sizes may be used, ranging from 1 to 1000 μm. Accordingly, the bead size may be about 1, 2, 3, 4, 5, 6, 7, 8, 9, 10, 15, 20, 25, 30, 35, 40, 45, 50, 60, 70, 80, 90, 100, 200, 300, 400, 500, 750 or 1000 μm. In an exemplary embodiment, the bead size is about 10 μm.

To facilitate detection of the antibody-peptide complex, an appropriate detectable label may be utilized. There are many different labels and methods of labeling known to those of ordinary skill in the art. Examples of the types of labels which may be used in the present invention include enzymes, radioisotopes, fluorescent compounds, colloidal metals, chemiluminescent compounds, phosphorescent compounds, and bioluminescent compounds. Those of ordinary skill in the art will know of suitable labels, or will be able to ascertain such, using routine experimentation. The labeling moiety will be observable in conventional immunohistochemical detection techniques being, for example, a fluorescent dye such as fluorescein, a chemiluminescense reagent, a radioisotope, a colloidal label, such as colloidal gold or colored latex beads, an enzyme label, or any other known labeling complex.

As is known in the art, detectable labels may be used to tag any member of the antibody-peptide complex, either directly (e.g., direct binding) or indirectly (e.g., secondary antibody) to facilitate detection. Various methods are known in the art to detect binding of the peptide with the antibody via a suitable detectable label. Detection may be by any method known in the art, such as immunologic techniques including immunoassays and the like. For example, detection of the antibody-peptide complex may be determined by techniques such as, but not limited to, Western blot analysis, flow cytometry, enzyme-linked immunosorbent assay (ELISA), radioimmunoassay (RIA), competition immunoassay, dual antibody sandwich assay, chemiluminescent assay, bioluminescent assay, fluorescent assay, and agglutination assay.

As discussed further in the following examples, beads used as solid supports may be modified by incorporation of nanoparticles. As used herein, the term "nanoparticle" refers to any particle having a diameter of less than 1000 nanometers (nm). In various embodiments, nanoparticles can be optically or magnetically detectable. For example, intrinsically fluorescent or luminescent nanoparticles, nanoparticles that comprise fluorescent or luminescent moieties, plasmon resonant nanoparticles, and magnetic nanoparticles are among the detectable nanoparticles that can be used in various embodiments of the present invention. Typically the nanoparticles have a diameter of 200 nm or less. In various embodiments, the nanoparticles have a diameter of about 100, 50, 40 or 30 nm or less, such as about 5 to 25 nm. In various embodiments, the nanoparticles are quantum dots, such as bright, fluorescent nanocrystals with physical dimensions small enough such that the effect of quantum confinement gives rise to unique optical and electronic properties. In various embodiments, optically detectable nanoparticles may be metal nanoparticles.

In various embodiments, the nanoparticles can have magnetic properties. For example, magnetization of the beads allows for one to use automated handling technologies to wash and manipulate the beads during the detection process. Additionally when dealing with fewer beads, it is easier to recover a greater number of beads for measurement when the beads are magnetized. Because one can use a lower number of beads, the signal per bead is higher, thus improving the signal response and thus increasing sensitivity. Additionally, fluorescence modification allows for tagging of multiple bead/antibody assays. Beads with known amounts of antibody may be added and to implement internal standards to improve the reliability of the resultant measurement. Furthermore, multiplex antibody detection is possible.

As used herein, magnetic nanoparticles refer to magnetically responsive particles that contain one or more metals or oxides or hydroxides thereof. Magnetically responsive materials of interest in this invention include paramagnetic materials, ferromagnetic materials, ferrimagnetic materials, and metamagnetic materials. As magnetic nanoparticles, any particles can be used, so long as the particles can be dispersed or suspended in an aqueous medium and can be separated from a dispersion liquid or a suspension through application of a magnetic field. Magnetic nanoparticles may include, for example, a salt, oxide, boride or sulfide of iron, cobalt or nickel; and rare earth elements having high magnetic susceptibility (e.g., hematite and ferrite). Specific examples of such magnetic nanoparticles that can also be used herein include iron, nickel, and cobalt, as well as metal oxides such as $Fe_3O_4$, $BaFe_{12}O_{19}$, $CoO$, $NiO$, $Mn_2O_3$, $Cr_2O_3$, and $CoMnP$. Additional examples of iron oxides particularly include a magnetite, a maghemite, and a mixture thereof.

In embodiments of the present invention wherein the solid support is a magnetic bead, the quantity of magnetically responsive material in the bead is not critical and can vary over a wide range. The quantity can affect the density of the bead, however, both the quantity and the particle size can affect the ease of maintaining the bead in suspension for purposes of achieving maximal contact between the liquid and solid phase and for facilitating flow cytometry. Furthermore, an excessive quantity of magnetically responsive material in the bead will produce autofluorescence at a level high enough to interfere with the assay results. It is therefore preferred that the concentration of magnetically responsive material be low enough to minimize any autofluorescence emanating from the material. With these considerations in mind, the magnetically responsive material in a bead in accordance with this invention preferably ranges from about 1% to about 75% by weight of the particle as a whole. A more preferred weight percent range is from about 2% to about 50%, a still more preferred weight percent range is from about 3% to about 25%, and an even more preferred weight percent range is from about 5% to about 15%. The magnetically responsive material can be dispersed throughout the polymer, applied as a coating on the polymer surface or as one of two or more coatings on the surface, or incorporated or affixed in any other manner that secures the material in the polymer matrix.

Multiplexing with the use of beads is achieved with this invention by assigning the beads to two or more groups, each group performing a separate assay and separable from the other group(s) by a "differentiation characteristic" which, as used herein, denotes a distinguishable characteristic that permits separate detection of the assay result in one group from that in another group.

In one embodiment, a differentiation characteristic that can be used to distinguish among the various groups of beads is fluorescence. Differentiation is accomplished by incorporating various fluorescent materials in the particles, the various fluorescent materials having different fluorescent emission spectra and being distinguishable on this basis. Fluorescence can be used both as a means of distinguishing the groups from each other and as a means of detection for the assay performed on the bead. The use of fluorescent materials with different emission spectra can be used as a means of distinguishing the groups from each other and as a means of distinguishing the group classification from the assay detections.

In related embodiments, differentiation characteristic that can be used to distinguish among the various groups of particles are light scatter or combinations of light scatter and emission. As discussed, light emission can be varied by incorporating fluorescent materials in the beads and using fluorescent materials that have different fluorescence intensities or that emit fluorescence at different wavelengths, or by varying the amount of fluorescent material incorporated. By using a plurality of fluorescent emissions at various wavelengths, the wavelength difference can be used to distinguish the particle groups from each other and also to distinguish the labels indicating the occurrence of binding reactions in the assay from the labels that identify the particle groups.

In various embodiments, the beads may have two or more fluororescent materials incorporated with the bead such that each bead in the array will have at least three distinguishable parameters associated with it (e.g., side scatter together with fluorescent emissions at two separate wavelengths). Thus, each bead can contain a plurality of fluorescent dyes at varying wavelengths.

In a related embodiment, a differentiation characteristic that can be used to distinguish among the various groups of beads is the bead size. For example, the groups are defined by nonoverlapping subranges of size. The beads may be sized to fall into two or more subranges, each selectively active in a single assay and inert relative to the other assays simultaneously being performed or detected. For example, beads of one size may include peptides including mimetopes that bind one antibody, while beads of another size may include peptides including mimetopes that bind a different antibody.

In another embodiment, a differentiation characteristic that can be used to distinguish among the various groups of beads is absorbance. In another embodiment, a differentiation characteristic that can be used to distinguish among the various groups of beads is the number of beads in each group. The number of particles of each group in an assay is varied in a known way, and the count of beads having various assay responses is determined. The various responses are associated with a particular assay by the number of particles having each response.

As is generally known in the art, other methods of detection may be utilized that do not incorporate labels, per se. For example, detection of surface plasmons generated by light denoted as a surface plasmon resonance (SPR) for planar surfaces or localized surface plasmon resonance (LSPR) for nanometer-sized metallic structures may be used to detect complexed antibody-peptide conjugates. Using such methods, a solid surface including a metal and bound peptides may be used to detect the binding event between antibody and peptide. Additional detection methods include surface enhanced raman scattering (SERS) for detection of the peptide-antibody interaction (Rohr et al., *Analytical Biochemistry*, 182:388-398, 1989).

When the distinguishable bead characteristic is a fluorescent dye or color, it can be coated on the surface of the bead, embedded in the bead, or bound to the molecules of the bead material. Thus, fluorescent beads can be manufactured by combining the polymer material with the fluorescent dye, or by impregnating the bead with the dye. Beads with dyes already incorporated are commercially available.

The assay performed at the surfaces of beads within a single group of particles can be any type of heterogeneous assay that yields a result differentiating a certain antibody from others in the sample. In various embodiments, immunometric or sandwich assays, are performed by using magnetically responsive beads to which are bound peptides including a mimetope that specifically binds an antibody. In this case, the bound peptides are present in excess relative to the suspected quantity range of the antibody so that all of the antibody binds. The beads are placed in contact with the sample, and simultaneously or sequentially, a second antibody conjugated to a detectable label specific for the peptide, antibody or antibody-peptide complex is added, the second antibody binding in a non-interfering manner. After a suitable incubation period, the liquid mixture including suspended beads is placed under the influence of a magnetic field, causing the beads to adhere to the walls of the reaction vessel, and the liquid phase is removed. The beads, still adhering to the vessel wall, are then washed to remove excess amounts of the second, labeled antibody that have not become bound to the immobilized peptide-antibody complex, and the beads are then resuspended in a carrier liquid for introduction into a flow cytometer for detection.

Instrumentation and methods of performing flow cytometry are known in the art, and used in the practice of the present invention. Flow cytometry includes the passage of a suspension of beads as a stream past a light beam and electro-optical sensors, in such a manner that only one particle at a time passes through the region. As each particle passes this region, the light beam is perturbed by the presence of the particle, and the resulting scattered and fluorescent light are detected. The optical signals are used by the instrumentation to identify the subgroup to which each particle belongs, along with the presence and amount of label, so that individual assay results are achieved.

Similarly, methods of and instrumentation for applying and removing a magnetic field as part of an automated assay are known to those skilled in the art.

In embodiments in which beads are used as the solid support and detection is performed by flow cytometry, beads that emit high autofluorescence should be avoided since this renders them unsuitable for flow cytometry. Particles created by standard emulsion polymerization techniques from a wide variety of starting monomers generally exhibit low autofluorescence. Conversely, particles that have been modified to increase porosity and therefore surface area (such particles are referred to in the literature as "macroporous" particles) exhibit high autofluorescence.

As used herein, the terms "sample" and "biological sample" refer to any sample suitable for the methods provided by the present invention. In one embodiment, the biological sample of the present invention is a physiological fluid, for example, whole blood or fraction thereof (e.g., serum or plasma), urine, spinal fluid, saliva, ejaculate and stool.

ELISA assays for serum or plasma antibody levels are typically limited by the need to dilute the sample to lower background. This was the case for the peptide ELISA described herein as well. However, the peptide bead based assay allowed for a specific assay with an unexpectedly low background binding, even in high concentrations of serum.

The assays described herein allow for specific detection of antibodies at low concentrations in a fluid sample. Detection may be achieved at antibody concentrations down to about 50, 40, 30, 20, 10, 5, or even 0.5 ng/ml, such as concentrations less than about 1000, 750, 500, 400, 300, 200, 100, 75, 50, 40, 30, 20, 10, 5 or even 0.5 ng/ml.

The methods described herein relating to detection of antibodies are particularly relevant to diagnostic and/or prognostic assays as relates to treatment and prevention of diseases, such as cancer. Many diagnostic, prognostic and/or monitoring assays rely on detection of a biological marker of a particular disease state or disease susceptibility. Such biological markers are commonly proteins or polypeptides that are characteristic of a particular disease or associated with susceptibility to disease.

Detection of specific antibodies may be used diagnostically or prognostically to assess the disease state or other factors, such as disease progression. Antibodies, typically serve as biological markers of disease or disease susceptibility. For example, autoantibodies are naturally occurring antibodies directed to an antigen which an individual's immune system recognizes as foreign even though that antigen actually originated in the individual. They may be present in the circulation as circulating free autoantibodies or in the form of circulating immune complexes consisting of autoantibodies bound to their target marker protein. Accordingly, detection of antibodies is important to assays which measure the immune response of an individual to the presence of tumor marker protein in terms of autoantibody production. Assay methods based on the detection of autoantibodies may therefore be of particular value early in the disease process and also in relation to screening of patients, for example in screening to identify individuals at risk of developing disease. In addition detection of autoantibodies may be of particular value for earlier detection of recurrent disease.

The assays described herein are also useful in selecting or monitoring therapies for a disease. For example, detection of specific antibodies may also be used diagnostically or prognostically to determine status and progression of a disease in patients undergoing treatment with a therapeutic antibody (e.g., the amount of unbound circulating antibody therapeutic may be correlated with disease progression, the ability to detect unbound).

The following examples are provided to further illustrate the embodiments of the present invention, but are not intended to limit the scope of the invention. While they are typical of those that might be used, other procedures, methodologies, or techniques known to those skilled in the art may alternatively be used.

Example 1

Assay Reagent Preparation

While the following assay reagent protocol is described using specifically identified reagents, such as specific fluorescent labels, specific phage-displayed libraries and generation of specifically identified peptides, the methods described herein may be utilized to generate peptides including mimetopes that interact with any antibody.

Antibodies were prepared as follows. Alemtuzumab (Genzyme, Cambridge, Mass.) and rituximab (Genentech, San Francisco, Calif.) were obtained from the UCSD Cancer Center pharmacy. The antibodies were fluorescently labeled using the Zenon® R-Phycoerythrin Human IgG labeling kit, Zenon® Alexa Fluor® 488 Human IgG labeling and Zenon® Alexa Fluor® 488 protein labeling kits (Invitrogen, Carlsbad, Calif.). For kinetic studies, Fab fragments of each mAb were prepared by papain digestion using a Fab preparation kit (Thermo Fisher Scientific, Rockford, Ill.) as per manufacturers instructions.

Peptide mimetopes were generated by screening phage-display libraries. Three phage-displayed peptide libraries (Ph.D.™ 7, Ph.D.™ 12, and Ph.D.™ C7C, New England Biolabs, Ipswich, Mass.) were combined and screened against the mAbs as previously described (Messmer et al., *J. Immunol.* 162(4):2184, 1999). Briefly, the mAbs were coated onto ELISA plates at a concentration of 1 ug/ml and incubated at 4° C. overnight. The coating solution was removed and the wells blocked with 2.5% bovine serum albumin (BSA) in tris buffered saline (TBS). After 1 hour at 4° C. the blocking solution was removed, the wells washed three times, and the phage libraries added in a final volume of 100 ul in TBS. After 1 hour incubation at room temperature the wells were washed with TBS ten times and the bound phage eluted for 10 minutes with 0.2M Glycine-HCl (ph 2.2). The eluted phage were neutralized with Tris-HCl (ph 9.1) and grown on K91 bacteria overnight. The bacteria were pelleted, the culture supernatant passed through a 0.2 um syringe tip filter, and the phage precipitated with 2.5M NaCl—20% polyethylene glycol (PEG). The phage pellet was resuspended in TBS and the next round of selection done as above. After the final round of selection, individual phage clones were picked and sequenced using the −96 III primer provided with the library kits.

Peptides defining mimetopes identified through panning of the phage display libraries were prepared and conjugated with solid supports as follows. Peptides were ordered from Sigma-Genosys (St. Louis, Mo.). The alemtuzumab binding peptide, pCp-1, had a sequence ACGSLSPSSCGGGS (SEQ ID NO:6), which includes the identified sequence of Cp-1 (SEQ ID NO:1) with the addition of a short linker peptide. Biotinylated peptides pCp-1B had a sequence ACGSLSPSSCGGK (SEQ ID NO:7) and rituximab binding peptide, pRTX-10B, had a sequence ACPYSNPSLCGGK (SEQ ID NO:8). Both peptides were biotinylated via the C-terminal lysine to maintain the same anchoring orientation as was the case when the peptide was displayed on the phage protein. The peptides were purified to 95% and 82% respectively by the manufacturer.

Biotinylated peptides were conjugated to 96-well NeutrAvidin coated plates (Pierce, Rockford, Ill.) as discussed in Example 3.

Alternatively, peptides were synthesized directly on 10 μm TentaGel™ beads using convention SPPS methods. After direct synthesis on the beads, the peptides were uncleaved and retained binding specific binding characteristics. Peptide bead conjugates prepared by direct synthesis were obtained from Peptides International (Louisville, Ky.). The alemtuzumab-binding peptide beads, pCp-1T, had sequence ACGSLSPSSCGGGS (SEQ ID NO:9) and the rituximab-binding peptide beads, pRTX-10T, had sequence ACPTSNPSLCGGGS (SEQ ID NO:10). Both were acetylated at the N terminus and coupled to 10 μm TentaGel™ beads at the C terminus.

Example 2

Binding Kinetics Analysis Protocol

Kinetics of antibody-peptide binding were studied using SkiPro™ Biomolecular Interaction technology platform on a SkiPro™ interferometer equipped with a 2-channel flow cell and an autosampler (Silicon Kinetics Inc. San Diego, Calif.). All reagents were purchased from Sigma-Aldrich (St. Louis, Mo.). All peptides were incubated with oxidizing agent Sodium Tetrathionate at 10 mM in PBS for 1 hour immediately before binding experiments. Biotinylated peptides were diluted to 5 μM in PBS/0.05% BSA and immobilized on Streptavidin-coated SkiSensor™ Biochips for 10 minutes at 4 μl/min flow rate. That resulted in an Optical Path Difference shift (Δ OPD) of 5-6 nm. Concentration series of antibodies and antibody Fab fragments were prepared as twofold dilutions in PBS/0.05% BSA. Binding was carried out for 10 minutes followed by 20 minutes dissociation. For all sensorgrams reference channel data was subtracted from the sample channel. The resulting multi-concentration series of binding curves were globally fit to a single binding site association/dissociation model.

Example 3

Detection of Antibodies in Chronic Lymphoid Leukemia Cells

This example illustrates detection of antibodies (alemtuzumab and rituximab) in chronic lymphoid leukemia (CLL) cells and serum samples. The cells were used in blocking experiments to determine the ability of peptide mimetopes specific for the antibodies (alemtuzumab and rituximab) to inhibit the binding of the antibodies to the surface of the primary CLL cells.

After informed consent was obtained per the Declaration of Helsinki, blood samples were collected from patients at the University of California, San Diego (UCSD) Medical Center who satisfied diagnosis and immunophenotypic criteria for common B-cell CLL.

CLL cells ($10^5$/per well) were seeded into 96-well plates in 100 μl of X-Vivo™ medium (BioWhittaker, Walkersville, Md.), and incubated with Zenon® labeled alemtuzumab or rituximab prepared as described in Example I (0.5 µg/well) for 1 h on ice. Subsequently, cells were washed two times with 100 µl FACS-wash (PBS, 5% FCS and 0.5% sodium azide) and fixed with 100 µl with 3.7% formaldehyde in PBS.

Detection of antibodies (alemtuzumab and rituximab) in both CLL cells and serum was performed using ELISA and flow cytometry.

For detection of antibodies by ELISA, each well in a 96-well NeutrAvidin coated plate (Pierce, Rockford, Ill.) was coated with 100 µl of a solution of biotinylated peptide at 30 ng/ml in ddH$_2$O and incubated for 2 hours at room temperature. Wells were washed five times with TBS/0.05% Tween-20® (TBST) using an automated plate washer (Columbus Pro, Tecan, Durham, N.C.). Non-specific binding sites were blocked by incubation with 300 µl of 5% BSA/TBS for 2 h at room temperature. Wells were washed five times with TBST. Wells were filled with 100 µl of standard or sample. Standard curves were assayed in triplicate. Plates were incubated for 2 h at room temperature and then washed with TBST. 100 µl of goat anti-human IgG POD antibody (Jackson Immunoresearch, West Grove, Pa.) was added at dilution 1:5000 in TBST for 30 minutes at room temperature. Wells were washed ten times with TBST. 100 µl/well of Turbo™ B (Pierce) substrate was added and incubated for 15-45 minutes. Reaction was stopped with 100 µl of 1M sulfuric acid and the absorbance was measured at 450 nm on an Infinite™ M200 plate reader (Tecan). For peptide blocking experiments, the antibody was pre-incubated with 12.5 µg/ml of the free peptide.

For detection of antibodies by flow cytometry peptide-bead conjugates as described in Example 1, 6×10$^4$ beads/sample, were mixed with different concentrations of the respective labeled antibody for 16 h at 4° C. in a rotator. The beads were washed twice with phosphate buffered saline (PBS) by centrifugation at 14000 rpm for 2 min at room temperature and were resuspended in 100 µl of PBS. Beads were analyzed on a BD FACSCalibur™ (Becton Dickinson, Franklin Lakes, N.J.) and the data analyzed on FlowJo™ (Treestar, Ashland, Oreg.) software.

Example 4

Fluoromagnetic Bead Modification Protocol

This example illustrates modification of the beads to generate fluoromagnetic beads which allow for improvement in sensitivity, multiplexability and automation of antibody detection.

Magnetization of the beads allows for one to use automated handling technologies to wash and manipulate the beads during the detection process. Additionally when dealing with fewer beads, it is easier to recover a greater number of beads for measurement when the beads are magnetized. Because one can use a lower number of beads, the signal per bead is higher, thus improving the signal response and thus increasing sensitivity. Additionally, fluorescence modification allows for tagging of multiple bead/antibody assays. Beads with known amounts of antibody may be added and to implement internal standards to improve the reliability of the resultant measurement. Furthermore, multiplex antibody detection is possible.

Modified beads were generated using the following protocol. First, stabilized 6.5 (+/−3 nm) FeO nanoparticles (NP) in heptane were obtained from Sigma. The size was selected based on bead pore size determinations from enzyme assays on bead substrates in the literature. A biphasic solution with 500 ml of dimethylformamide (DMF) and 500 ml of FeO NP in heptane was created in a microcentrifuge tube. An external magnetic field was applied to drive the NP from the heptane phase to DMF. Next, the heptane phase was removed and then the DMF-NP solution was vigorously mixed. Fluorophores were then added to DMF-NP solution for incorporation into the beads, however, any reporter particle may be added (e.g., fluorophores, contrast agents, and the like). Next, 10 um beads were added to a new DMF solution and allowed to swell for 5 min. The fluorescently labeled DMF-NP solution was then added to DMF-beads and mixed vigorously. Next, the beads were pelleted in a centrifuge and half of the supernatant was removed and replaced with H$_2$O a total of 4 times. The beads were pelleted a final time and the entire supernatant was removed and replaced with H$_2$O. The beads were then filtered on an 8 um filter to remove any non-bead materials.

The beads were then analyzed to ensure modification of the beads. Bead movement was observed upon exposure of the beads to a magnetic field. A mixture of beads was generated which included magnetic beads labeled with four different fluorescent colors. Sample analysis were performed in which the crosstalk signal from other fluorophores was subtracted. In doing so, it was possible to unambiguously determine which beads corresponded to which label.

Modified fluoromagnetic beads generated using the protocol above were also incubated with fluorescently labeled antibody. Binding of the beads with the corresponding antibody was observed using flow cytometry confirming that antibody reactivity was still present after modification of the beads. Additionally, modified fluoromagnetic beads including peptide mimetopes specific for rituximab were incubated with alemtuzumab and analyzed to determine whether rituximab specific antigen beads cross reacted with alemtuzumab. Upon analysis, no cross-reactivity was observed.

Figures 9A, 9B:
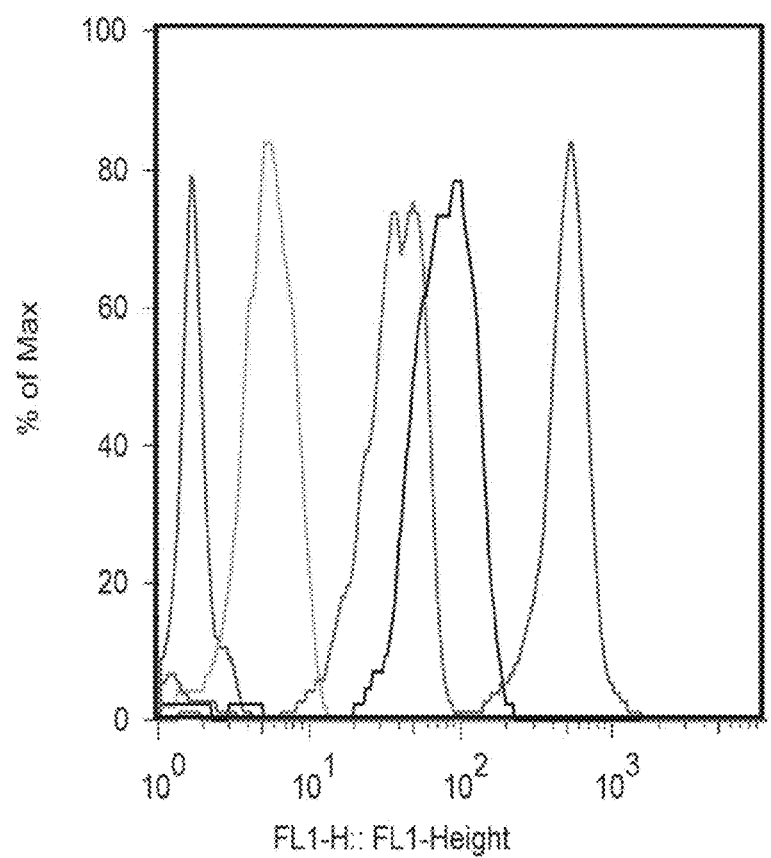
FIG. 9A is a graphical illustration showing detection of red fluoromagnetic beads specific for alemtuzumab detection at various concentrations. Fluorescence intensities of 0 ug/ml, 0.1 ug/ml, 0.5 ug/ml, 1.0 ug/ml, and 10.0 ug/ml of the fluoromagnetic beads are shown in a spiked PBS solution with 3% BSA.
FIG. 9B is a table showing the results of the analysis in FIG. 9A.
Figure 10A:
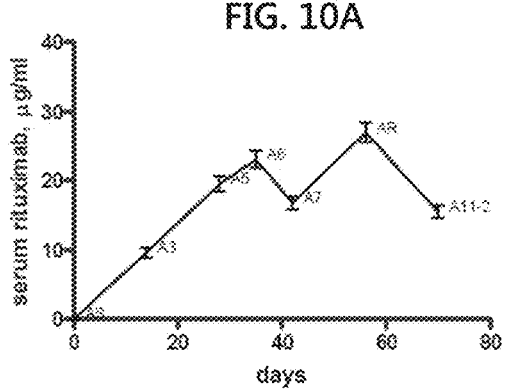
Figure 10B:
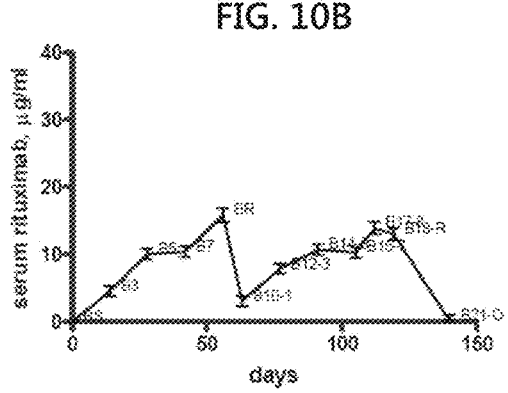
Figure 10C:
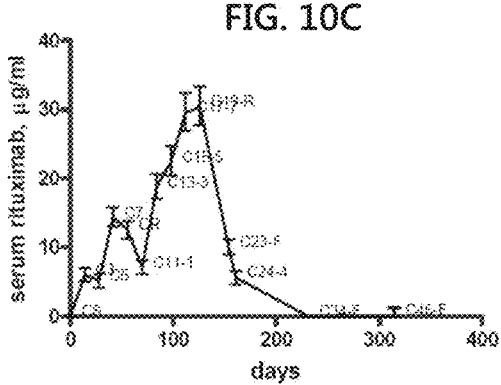
Figure 10D:
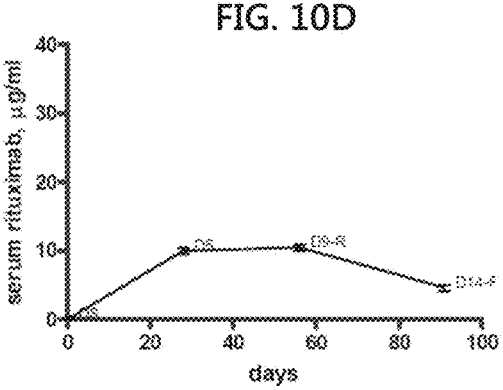
Figure 10E:
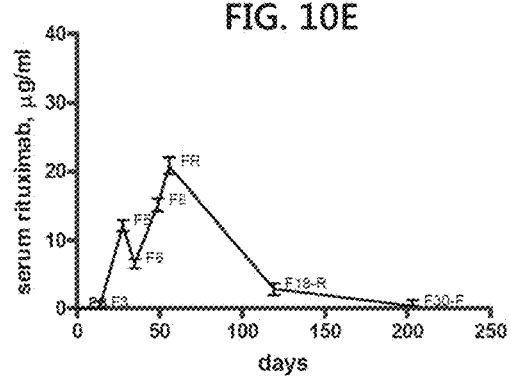
Figure 10F:
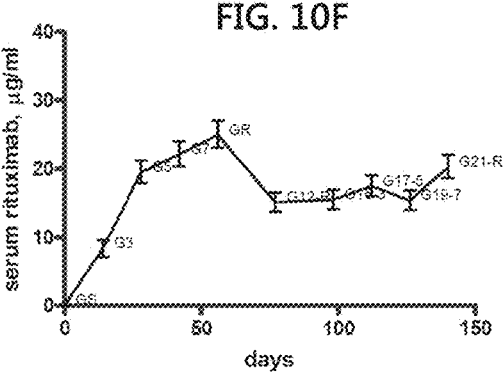

Further, detection of the modified fluoromagnetic beads was observed at low concentrations of the beads. For example, as shown in FIGS. 9A and 9B, detection of fluoromagnetic beads specific for alemtuzumab was possible down to concentrations of about 0.1 ug/ml of beads in BSA+PBS solution. FIGS. 9A and 9B show fluorescence intensities of 0 ug/ml, 0.1 ug/ml, 0.5 ug/ml, 1.0 ug/ml, and 10.0 ug/ml of the fluoromagnetic beads in a spiked PBS solution with 3% BSA.

Example 5

Detection of Rituximab and Alemtuzumab

A pool of three phage displayed peptide libraries was panned against rituximab or alemtuzumab. In each case, significant enrichment in the number of bound and recovered phage was observed after three rounds. Individual phage plaques were selected from the final enriched population and determined the sequence of the displayed peptides (FIG. 1). Interestingly, all of the peptides recovered were from the cysteine containing library. The rituximab-binding peptide sequences were identical to those identified in a previous report (Perosa et al., *J. Immunol.* 179(11):7967, 2007). The alemtuzumab-binding sequences shared a motif and were similar in sequence to the extra-cellular domain of CD52 (Hale, *Immunotechnology* 1(3-4):175, 1995). Phage displaying either the rituximab or alemtuzumab binding peptides were specific for the cognate antibody and did not bind the other or normal human IgG (data not shown).

Alemtuzumab binding sequence Cp-1 (SEQ ID NO:1) and rituximab binding sequence RTX-10 (SEQ ID NO:5) were chosen for further analysis. Biotinylated peptides were used for kinetic binding measurements using nano-pore optical interferometry (FIGS. 7A-7D). The binding kinetic parameters thus determined are shown in Table I.

TABLE I

Binding Kinetic Parameters

| | Whole molecule | | Fab | |
|---|---|---|---|---|
| | RTX-10 | Cp-1 | RTX-10 | Cp-1 |
| Kon, M-1*s-1 | 7.51E+03 | 8.13E+03 | 1.63E+03 | 2.46E+03 |
| Koff, s-1 | 9.84E-04 | 1.32E-03 | 6.51E-03 | 5.05E-03 |
| Kd | 131 nM | 163 nM | 3.99 µM | 2.05 µM |

The Kd for both peptide-mAb pairs was 100-200 nM when the intact mAb molecules were used, but when Fab fragments were used the $K_d$ was 2-4 uM. This suggested that surface immobilized peptides are capable of bivalently interacting with the two Fab regions of the intact molecule, producing a greater binding avidity than the monovalent Fab-peptide interaction.

To determine if the peptides were binding to the antigen binding region of the mAbs, soluble synthetic peptides were evaluated for their ability to inhibit the binding of alemtuzumab and rituximab to the surface of primary chronic lymphocytic leukemia (CLL) cells (FIGS. 2A and 2B). Each peptide significantly inhibited the binding of the respective mAb to the CLL cells. There was no effect on the binding activity of the other mAb (data not shown). This result indicted that the peptides could be used for detection of free, active mAb.

Figure 3B:
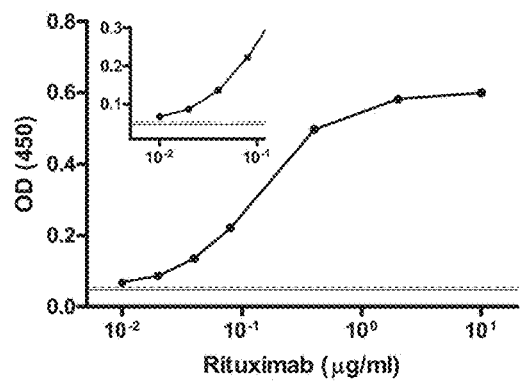
Figure 4:
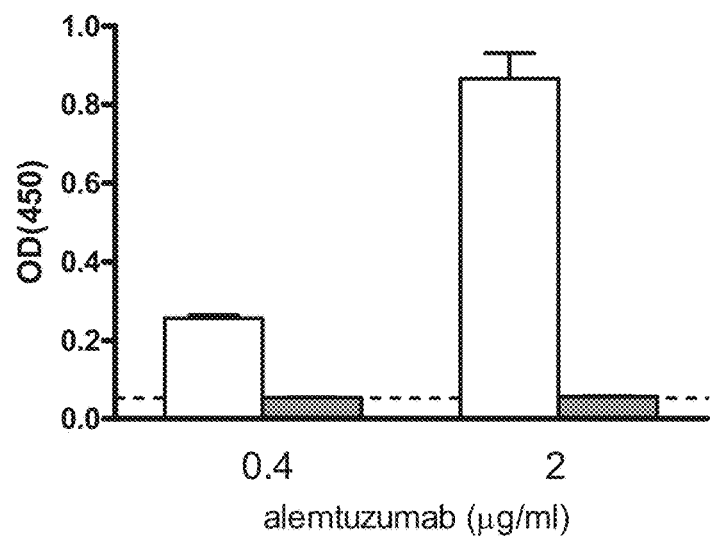
FIG. 4 is a graphical illustration showing soluble peptide inhibition of alemtuzumab peptide ELISA. At 0.4 and 2.0 ug/ml, alemtuzumab produces a strong ELISA signal (open bars). When preincubated with the soluble peptide pCp-1 (SEQ ID NO: 6) (filled bars), the signal was reduced to the background level with no alemtuzumab (dashed line).

Neutravidin plates were coated with biotinylated peptides for an ELISA following the protocol in Example 3. Representative titration curves for each mAb in saline buffer are shown in FIGS. 3A and 3B. The limit of detection was approximately 10 ng/ml. The binding of the mAb to the peptide coated plates could be completely inhibited by an excess of soluble peptide (FIG. 4). However, when diluted serum was used instead of saline buffer, the assay sensitivity was compromised by higher backgrounds that required dilutions of the serum sample by at least 100 fold. The functional sensitivity of the assay was thus approximately 1 ug/ml.

Figure 6A:
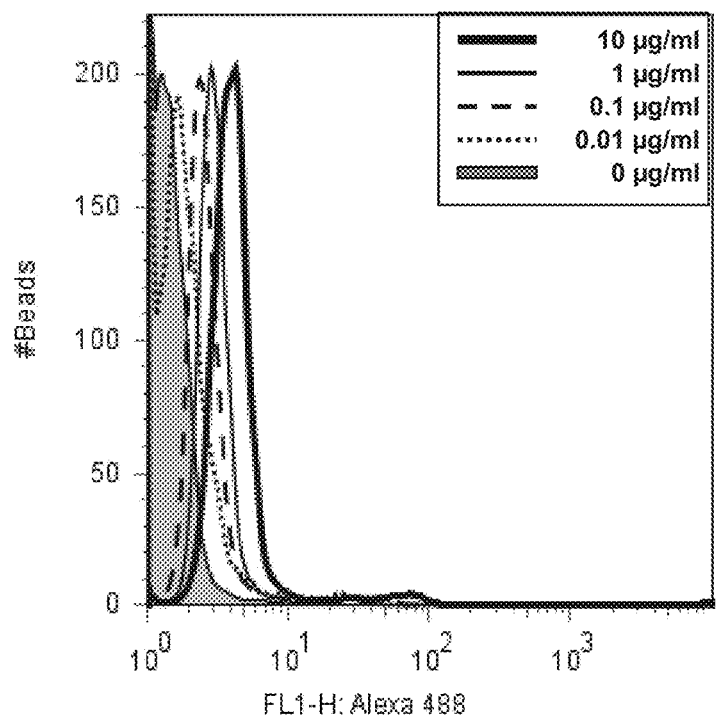
FIGS. 6A and 6B include graphical illustrations showing alemtuzumab bead titrations. Different concentrations of alemtuzumab in 10 µl of inactivated serum were analyzed by flow cytometry using pCp-1T (SEQ ID NO: 9) conjugated beads. Alemtuzumab (Campath™) bead complexes were labeled using Alexa Fluor 488™.
Figure 6B:
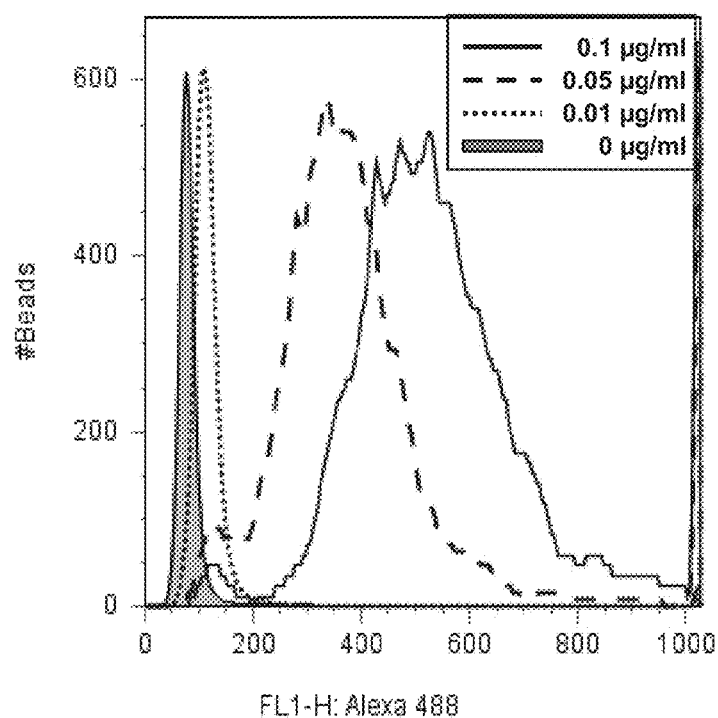
Figure 7A:
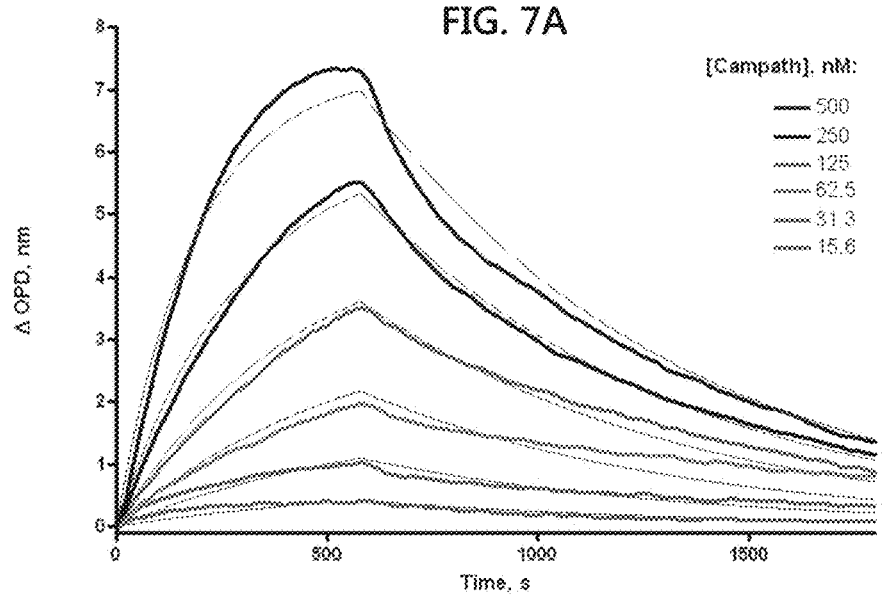
FIGS. 7A to 7D include graphical illustrations showing the kinetics of antibody-peptide binding. Biotinylated peptides were captured onto streptavidin coated nanoporous surfaces. The binding of the mAb or their Fab fragments was monitored on a SkiPro™ interferometer. The binding curves were globally fit to a single binding site association/dissociation model to derive Kon, Koff, and Kd values.
Figure 7B:
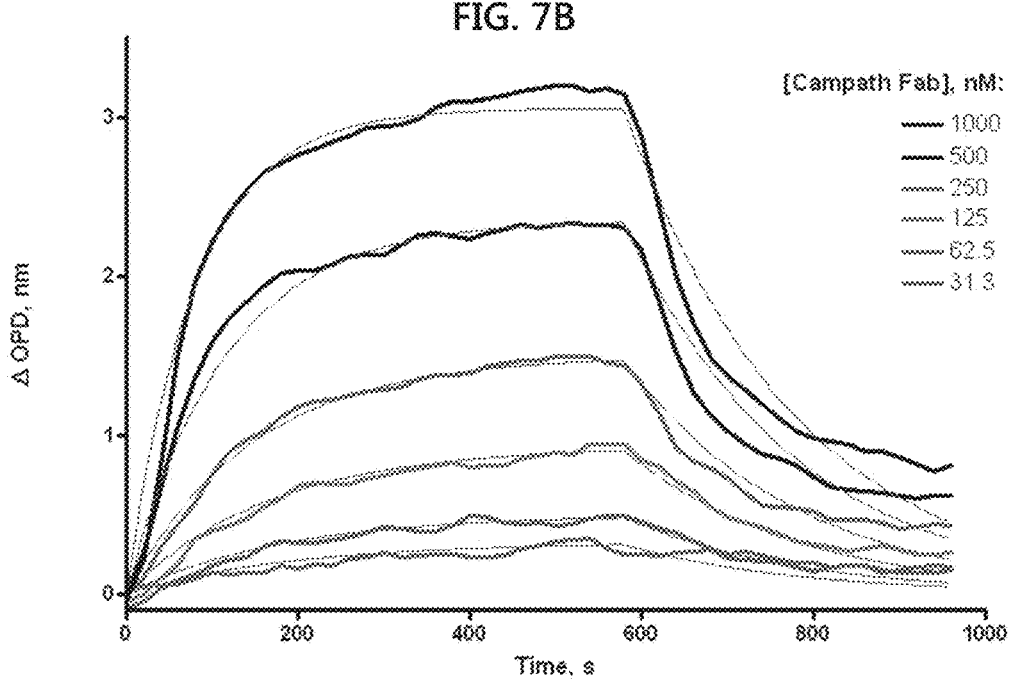
Figure 7C:
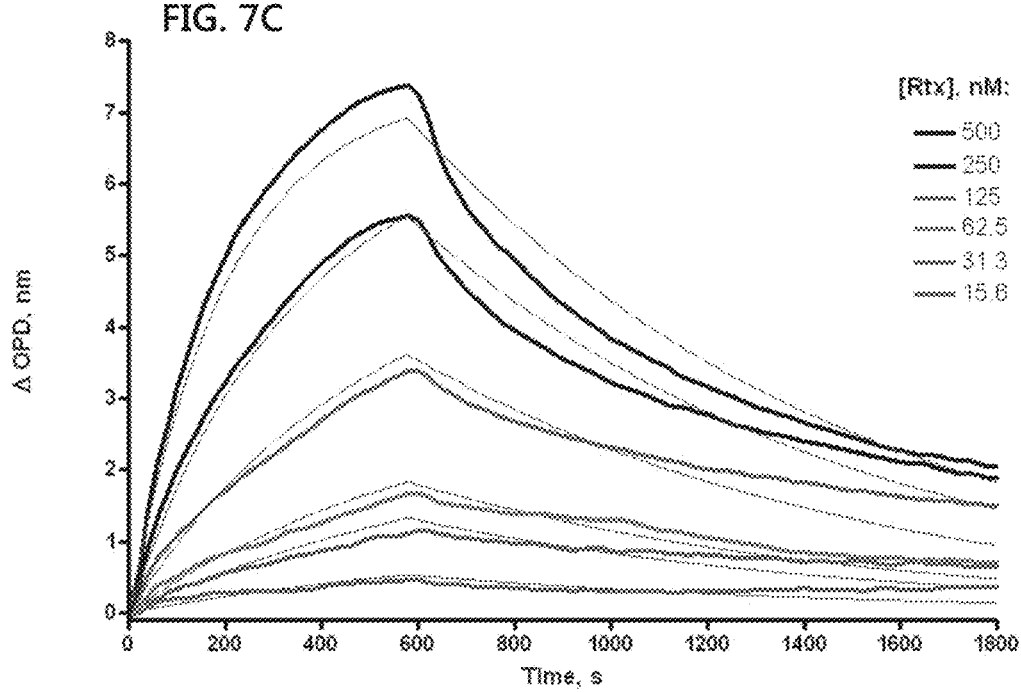
Figure 7D:
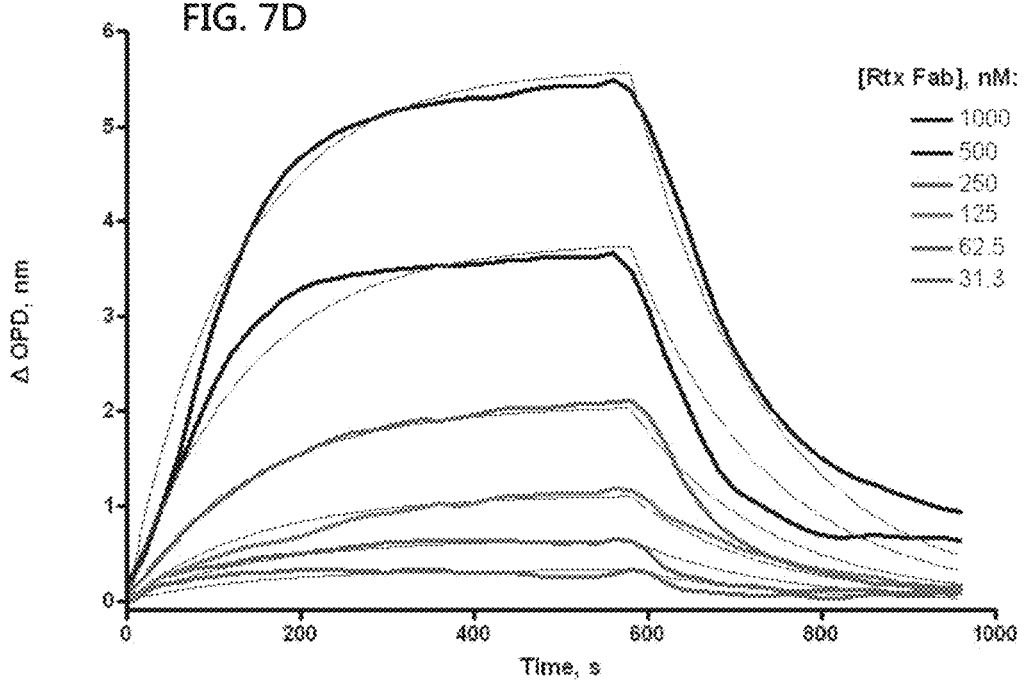

To mitigate the problem of high background signals when measuring mAb in serum or plasma, a bead based assay was developed as discussed in Example 3. The rituximab and alemtuzumab peptides were synthesized on 10 µm diameter tentagel beads, hereafter known as pCp-1T (SEQ ID NO:9) and pRTX-10T (SEQ ID NO:10). TentaGel™, a PEG polystyrene co-polymer, is a common solid phase synthesis support material and commercially prepared peptides are typically cleaved from the surface of such beads. Specific cognate antibody binding was confirmed by flow cytometry and fluorescent microscopy (FIGS. 5A-5C). Alemtuzumab was titrated into normal human serum and incubated with the pCp-1T (SEQ ID NO:9) beads. After washing and addition of a fluorescent secondary anti-human IgG antibody, the fluorescence on the beads was quantitated by flow cytometry as shown in Example 3. The fluorescent signals correlated with the alemtuzumab concentration, with very little background from serum alone (FIGS. 6A and 6B). Specific detection of alemtuzumab was achieved at concentrations as low as 50 ng/ml, an order of magnitude improvement over the currently used assays that require the mAb to be present at concentrations above 500 ng/ml in biologic samples (Rebello et al., *J. Immunol. Methods* 260(1-2):285, 2002).

Example 6

Detection of Uncomplexed Rituximab in Serum

Analysis and detection of uncomplexed rituximab in serum of CLL patients being treated with rituximab was performed using the methods described herein. Serum was obtained from CLL patients being treated with rituximab over at various timepoints during ongoing treatment. The results are shown in FIGS. 10A-L which show plots of serum rituximab concentration at different time points for a given.

Example 7

Generation of Peptides Including Mimetopes for Monoclonal Antibodies

Peptides including mimetopes for additional monoclonal antibodies were produced by screening phage display peptide libraries as discussed herein. FIG. 8 is an illustration showing phage displayed peptide sequences recovered from panning against three different mAbs. Phage-displayed peptide sequences recovered from panning against bevacizumab (Avastin™) included Avastin™-02 (SEQ ID NO:11), Avastin™-01 (SEQ ID NO:12), Avastin™-05 (SEQ ID NO:13), and Avastin™-07 (SEQ ID NO:14). Phage-displayed peptide sequences recovered from panning against trastuzumab (Herceptin™) included Herceptin™-01 (SEQ ID NO:15). Phage-displayed peptide sequences recovered from panning against zanolimumab (HuMax™) included HuMax™-01 (SEQ ID NO:16), HuMax™-04 (SEQ ID NO:17), HuMax™-05 (SEQ ID NO:18), and HuMax™-06 (SEQ ID NO:19). Phage-displayed libraries were panned against the monoclonal antibodies for 4 rounds, after which individual phage clones were picked and sequenced.

Although the invention has been described with reference to the above example, it will be understood that modifications and variations are encompassed within the spirit and scope of the invention. Accordingly, the invention is limited only by the following claims.

What is claimed is:

1. A complex comprising a therapeutic monoclonal antibody and a peptide, said complex comprising:
   a) a therapeutic monoclonal antibody which is not complexed to an epitope of a target protein; and
   b) a peptide comprising an amino acid sequence selected from the group consisting of SEQ ID NOs: 1-3, wherein the peptide is complexed to said therapeutic monoclonal antibody, said peptide having a length of about 5-15 amino acids and comprising a mimetope recognized by the therapeutic monoclonal antibody,
wherein the mimetope comprises a linear sequence of amino acids which is different than a linear sequence of amino acids in the epitope of the target protein, wherein the therapeutic monoclonal antibody is alemtuzumab obtained from the circulation of a subject undergoing alemtuzumab treatment, and wherein the peptide is attached directly on a solid support.

2. The complex of claim 1, wherein the mimetope binds to the antigen binding site of the therapeutic monoclonal antibody.

3. The complex of claim 1, wherein the therapeutic monoclonal antibody which is not complexed to an epitope of a target protein is present in a biological sample obtained from a subject.

4. The complex of claim 2, wherein the uncomplexed therapeutic monoclonal antibody is at concentrations from about 50 ng/ml to about 500 ng/ml.

5. The complex of claim 1, wherein the mimetope is identified from a phage-displayed phage library.

6. The complex of claim 1, further comprising a detectable label on the therapeutic monoclonal antibody or the peptide.

7. The complex of claim 6, wherein the detectable label is detectable by a method selected from the group consisting of: Western blot analysis, flow cytometry, enzyme-linked immunosorbent assay (ELISA), radioimmunoassay (RIA), competition immunoassay, dual antibody sandwich assay, chemiluminescent assay, bioluminescent assay, fluorescent assay, and agglutination assay.

8. The complex of claim 3, wherein the biological sample is a fluid.

9. The complex of claim 1, wherein the solid support is a bead.

10. The complex of claim 9, wherein the bead is magnetic.

11. The complex of claim 9, wherein the bead comprises magnetic nanoparticles.

12. The complex of claim 11, wherein the magnetic nanoparticles comprise iron oxide (FeO).

13. The complex of claim 11, wherein the bead has a particle size of about 1 μm to 50 μm.

14. The complex of claim 13, wherein the bead has a particle size of about 10 μm.

15. The complex of claim 11, wherein the bead further comprises a fluorophore.

16. The complex of claim 3, wherein the subject is a human subject.

17. The complex of claim 3, wherein the complex comprises a therapeutic monoclonal antibody which is present at concentrations below 500 ng/ml in the biological sample.

* * * * *

SEQUENCE LISTING

<160> NUMBER OF SEQ ID NOS: 19

<210> SEQ ID NO 1
<211> LENGTH: 10
<212> TYPE: PRT
<213> ORGANISM: Artificial Sequence
<220> FEATURE:

<223> OTHER INFORMATION: Synthetic construct

<400> SEQUENCE: 1

Ala Cys Gly Ser Leu Ser Pro Ser Ser Cys
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Synthetic construct

<400> SEQUENCE: 2

Ala Cys Lys Ser Gln Ser Pro Ser Ala Cys
1               5                   10

<210> SEQ ID NO 3
<211> LENGTH: 10
<212> TYPE: PRT
<213> ORGANISM: Artificial Sequence
<220> FEATURE:
<223> OTHER INFORMATION: Synthetic construct

<400> SEQUENCE: 3

Ala Cys Gly Ser Thr Ser Pro Ser Ser Cys
1               5                   10

<210> SEQ ID NO 4
<211> LENGTH: 10
<212> TYPE: PRT
<213> ORGANISM: Artificial Sequence
<220> FEATURE:
<223> OTHER INFORMATION: Synthetic construct

<400> SEQUENCE: 4

Ala Cys Pro Tyr Ala Asn Pro Ser Met Cys
1               5                   10

<210> SEQ ID NO 5
<211> LENGTH: 10
<212> TYPE: PRT
<213> ORGANISM: Artificial Sequence
<220> FEATURE:
<223> OTHER INFORMATION: Synthetic construct

<400> SEQUENCE: 5

Ala Cys Pro Tyr Ser Asn Pro Ser Leu Cys
1               5                   10

<210> SEQ ID NO 6
<211> LENGTH: 14
<212> TYPE: PRT
<213> ORGANISM: Artificial Sequence
<220> FEATURE:
<223> OTHER INFORMATION: Synthetic construct

<400> SEQUENCE: 6

Ala Cys Gly Ser Leu Ser Pro Ser Ser Cys Gly Gly Gly Ser
1               5                   10

<210> SEQ ID NO 7
<211> LENGTH: 13
<212> TYPE: PRT
<213> ORGANISM: Artificial Sequence
<220> FEATURE:
<223> OTHER INFORMATION: Synthetic construct

<400> SEQUENCE: 7

Ala Cys Gly Ser Leu Ser Pro Ser Ser Cys Gly Gly Lys
1               5                   10

<210> SEQ ID NO 8
<211> LENGTH: 13
<212> TYPE: PRT
<213> ORGANISM: Artificial Sequence
<220> FEATURE:
<223> OTHER INFORMATION: Synthetic construct

<400> SEQUENCE: 8

Ala Cys Pro Tyr Ser Asn Pro Ser Leu Cys Gly Gly Lys
1               5                   10

<210> SEQ ID NO 9
<211> LENGTH: 14
<212> TYPE: PRT
<213> ORGANISM: Artificial Sequence
<220> FEATURE:
<223> OTHER INFORMATION: Synthetic construct

<400> SEQUENCE: 9

Ala Cys Gly Ser Leu Ser Pro Ser Ser Cys Gly Gly Gly Ser
1               5                   10

<210> SEQ ID NO 10
<211> LENGTH: 14
<212> TYPE: PRT
<213> ORGANISM: Artificial Sequence
<220> FEATURE:
<223> OTHER INFORMATION: Synthetic construct

<400> SEQUENCE: 10

Ala Cys Pro Thr Ser Asn Pro Ser Leu Cys Gly Gly Gly Ser
1               5                   10

<210> SEQ ID NO 11
<211> LENGTH: 9
<212> TYPE: PRT
<213> ORGANISM: Artificial Sequence
<220> FEATURE:
<223> OTHER INFORMATION: Synthetic construct

<400> SEQUENCE: 11

Cys Ile Pro Ser Ile Arg Glu Trp Cys
1               5

<210> SEQ ID NO 12
<211> LENGTH: 9
<212> TYPE: PRT
<213> ORGANISM: Artificial Sequence
<220> FEATURE:
<223> OTHER INFORMATION: Synthetic construct

<400> SEQUENCE: 12

Cys Met Ser Pro Phe Asp His Ser Cys
1               5

<210> SEQ ID NO 13
<211> LENGTH: 9
<212> TYPE: PRT
<213> ORGANISM: Artificial Sequence
<220> FEATURE:
<223> OTHER INFORMATION: Synthetic construct

```
<400> SEQUENCE: 13

Cys Phe Leu Arg Ser Gly Leu Pro Cys
1               5

<210> SEQ ID NO 14
<211> LENGTH: 9
<212> TYPE: PRT
<213> ORGANISM: Artificial Sequence
<220> FEATURE:
<223> OTHER INFORMATION: Synthetic construct

<400> SEQUENCE: 14

Cys Thr Asp Thr Ala Thr Ala Leu Cys
1               5

<210> SEQ ID NO 15
<211> LENGTH: 9
<212> TYPE: PRT
<213> ORGANISM: Artificial Sequence
<220> FEATURE:
<223> OTHER INFORMATION: Synthetic construct

<400> SEQUENCE: 15

Cys Val Asp His His Leu Asp His Cys
1               5

<210> SEQ ID NO 16
<211> LENGTH: 9
<212> TYPE: PRT
<213> ORGANISM: Artificial Sequence
<220> FEATURE:
<223> OTHER INFORMATION: Synthetic construct

<400> SEQUENCE: 16

Cys Ala Pro Gly Phe Leu Pro Val Cys
1               5

<210> SEQ ID NO 17
<211> LENGTH: 9
<212> TYPE: PRT
<213> ORGANISM: Artificial Sequence
<220> FEATURE:
<223> OTHER INFORMATION: Synthetic construct

<400> SEQUENCE: 17

Cys Leu Trp Pro Pro Ser Pro Val Cys
1               5

<210> SEQ ID NO 18
<211> LENGTH: 9
<212> TYPE: PRT
<213> ORGANISM: Artificial Sequence
<220> FEATURE:
<223> OTHER INFORMATION: Synthetic construct

<400> SEQUENCE: 18

Cys Ser Trp Pro Pro Ser Pro Val Cys
1               5

<210> SEQ ID NO 19
<211> LENGTH: 9
<212> TYPE: PRT
<213> ORGANISM: Artificial Sequence
<220> FEATURE:
```

-continued

```
<223> OTHER INFORMATION: Synthetic construct

<400> SEQUENCE: 19

Cys Ser Tyr Pro Pro Ala Pro Val Cys
1               5
```